(12) United States Patent
McKiernan et al.

(10) Patent No.: US 8,419,701 B2
(45) Date of Patent: *Apr. 16, 2013

(54) ABSORBENT ARTICLES WITH STRETCH ZONES COMPRISING SLOW RECOVERY ELASTIC MATERIALS

(75) Inventors: Robin Lynn McKiernan, Mason, OH (US); Donald Carroll Roe, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 884 days.

This patent is subject to a terminal disclaimer.

(21) Appl. No.: 11/145,353

(22) Filed: Jun. 3, 2005

(65) Prior Publication Data

US 2006/0155255 A1  Jul. 13, 2006

Related U.S. Application Data

(60) Provisional application No. 60/643,920, filed on Jan. 10, 2005.

(51) Int. Cl.
*A61F 13/475* (2006.01)

(52) U.S. Cl.
USPC .................. 604/385.27; 604/385.24

(58) Field of Classification Search ............... 604/385.27
See application file for complete search history.

(56) References Cited

U.S. PATENT DOCUMENTS

| | | | |
|---|---|---|---|
| 3,086,242 A | | 4/1963 | Cook et al. |
| 3,139,468 A | | 6/1964 | Wheat |
| 3,370,630 A | * | 2/1968 | Haugh et al. ............... 383/21 |
| 3,587,581 A | | 6/1971 | Jones, Sr. |
| 3,592,946 A | | 7/1971 | Griffith |
| 3,601,923 A | | 8/1971 | Rosenberg |
| 3,639,917 A | | 2/1972 | Althouse |

(Continued)

FOREIGN PATENT DOCUMENTS

| | | |
|---|---|---|
| CH | 528285 | 2/1968 |
| DE | 1910911 | 3/1969 |

(Continued)

OTHER PUBLICATIONS

White, Liz, Viscoelastic foam mattresses: marketing hype or molecular miracle?, Urethanes Technology: vol. 18, No. 6: Dec. 2001/Jan. 2002.*

(Continued)

*Primary Examiner* — Melanie Hand
*Assistant Examiner* — Paula Craig
(74) *Attorney, Agent, or Firm* — Kathleen Y. Carter; John G. Powell; Richard L. Alexander

(57) ABSTRACT

An absorbent article may have at least one stretch zone comprising a slow recovery elastomer wherein the slow recovery elastomer exhibits a normalized unload force of greater than about 0.04 N/mm$^2$ at 37° C.; and the slow recovery elastomer exhibits at least about 20% post elongation strain at 22° C. after 15 seconds of recovery from a 400% strain. The absorbent article may additionally comprises one or more of a liquid permeable topsheet, a liquid impermeable backsheet, an absorbent core, an ear, a side panel, a waist feature, a fastener component, a leg cuff, a gasketing cuff, and a barrier cuff, wherein the feature comprises at least a part of the stretch zone.

22 Claims, 20 Drawing Sheets

U.S. PATENT DOCUMENTS

| | | | |
|---|---|---|---|
| 3,819,401 A | 6/1974 | Massengale et al. | |
| 3,848,594 A | 11/1974 | Buell | |
| 3,860,003 A | 1/1975 | Buell | |
| 3,911,173 A | 10/1975 | Sprague, Jr. | |
| 3,912,565 A | 10/1975 | Koch et al. | |
| 3,929,135 A | 12/1975 | Thompson | |
| RE28,688 E | 1/1976 | Cook | |
| 4,023,571 A * | 5/1977 | Comerford et al. | 604/364 |
| 4,054,616 A | 10/1977 | Miki et al. | |
| 4,089,913 A | 5/1978 | Miki et al. | |
| 4,116,842 A | 9/1978 | Meier | |
| 4,122,134 A | 10/1978 | Miki et al. | |
| 4,152,370 A | 5/1979 | Moczygemba | |
| 4,169,336 A | 10/1979 | Kuhn | |
| 4,248,981 A | 2/1981 | Milkovich et al. | |
| 4,248,982 A | 2/1981 | Bi et al. | |
| 4,248,984 A | 2/1981 | Bi et al. | |
| 4,259,220 A | 3/1981 | Bunnelle et al. | |
| 4,324,246 A | 4/1982 | Mullane et al. | |
| 4,337,771 A | 7/1982 | Pieniak et al. | |
| 4,342,314 A | 8/1982 | Radel et al. | |
| 4,346,198 A | 8/1982 | Doak et al. | |
| 4,381,781 A | 5/1983 | Sciaraffa et al. | |
| 4,412,087 A | 10/1983 | Trepka | |
| 4,418,180 A | 11/1983 | Heinz et al. | |
| 4,450,026 A | 5/1984 | Pieniak et al. | |
| 4,463,045 A | 7/1984 | Ahr et al. | |
| 4,515,595 A | 5/1985 | Kievit et al. | |
| 4,573,986 A | 3/1986 | Minetola et al. | |
| 4,603,155 A | 7/1986 | Muramori et al. | |
| 4,609,191 A | 9/1986 | Remme | |
| 4,609,518 A | 9/1986 | Curro et al. | |
| 4,610,678 A | 9/1986 | Weisman et al. | |
| 4,629,643 A | 12/1986 | Curro et al. | |
| 4,636,207 A | 1/1987 | Buell | |
| 4,662,875 A | 5/1987 | Hirotsu et al. | |
| 4,673,402 A | 6/1987 | Weisman et al. | |
| 4,681,580 A | 7/1987 | Reising et al. | |
| 4,695,278 A | 9/1987 | Lawson | |
| 4,698,242 A | 10/1987 | Salerno | |
| 4,699,622 A | 10/1987 | Toussant et al. | |
| 4,699,941 A | 10/1987 | Salerno | |
| 4,704,115 A | 11/1987 | Buell | |
| 4,704,116 A | 11/1987 | Enloe | |
| 4,704,434 A | 11/1987 | Kitchen et al. | |
| 4,710,189 A | 12/1987 | Lash | |
| 4,719,261 A | 1/1988 | Bunnelle et al. | |
| 4,720,415 A | 1/1988 | Vander Wielen et al. | |
| 4,761,198 A | 8/1988 | Salerno | |
| 4,785,996 A | 11/1988 | Ziecker et al. | |
| 4,787,897 A | 11/1988 | Torimae et al. | |
| 4,795,454 A | 1/1989 | Dragoo | |
| 4,808,178 A | 2/1989 | Aziz et al. | |
| 4,816,025 A | 3/1989 | Foreman | |
| 4,816,094 A | 3/1989 | Pomplun et al. | |
| 4,820,590 A | 4/1989 | Hodgson, Jr. et al. | |
| 4,834,735 A | 5/1989 | Alemany et al. | |
| 4,842,666 A | 6/1989 | Werenicz | |
| 4,846,815 A | 7/1989 | Scripps | |
| 4,857,067 A | 8/1989 | Wood et al. | |
| 4,874,255 A * | 10/1989 | Ball et al. | 383/8 |
| 4,888,231 A | 12/1989 | Angstadt | |
| 4,892,536 A | 1/1990 | DesMarais et al. | |
| 4,894,060 A | 1/1990 | Nestegard | |
| 4,900,317 A | 2/1990 | Buell | |
| 4,909,803 A | 3/1990 | Aziz et al. | |
| 4,938,753 A | 7/1990 | VanGomyel et al. | |
| 4,939,208 A | 7/1990 | Lanza et al. | |
| 4,940,464 A | 7/1990 | Van Gompel et al. | |
| 4,946,527 A | 8/1990 | Battrell | |
| 4,963,140 A | 10/1990 | Robertson et al. | |
| 4,965,122 A | 10/1990 | Morman | |
| 4,968,312 A | 11/1990 | Khan | |
| 4,981,747 A | 1/1991 | Morman et al. | |
| 4,987,194 A | 1/1991 | Maeda et al. | |
| 4,988,344 A | 1/1991 | Reising et al. | |
| 4,988,345 A | 1/1991 | Reising | |
| 4,990,147 A | 2/1991 | Freeland | |
| 5,006,394 A | 4/1991 | Baird | |
| 5,026,364 A | 6/1991 | Robertson | |
| 5,028,646 A | 7/1991 | Miller et al. | |
| 5,036,978 A | 8/1991 | Frank et al. | |
| 5,037,416 A | 8/1991 | Allen et al. | |
| 5,047,484 A | 9/1991 | Tung | |
| 5,049,591 A | 9/1991 | Hayashi et al. | |
| 5,050,742 A | 9/1991 | Muckenfuhs | |
| 5,054,619 A | 10/1991 | Muckenfuhs | |
| 5,062,840 A | 11/1991 | Holt et al. | |
| 5,085,654 A | 2/1992 | Buell | |
| 5,089,558 A | 2/1992 | Hall et al. | |
| 5,092,861 A | 3/1992 | Nomura et al. | |
| 5,093,384 A | 3/1992 | Hayashi et al. | |
| 5,098,776 A | 3/1992 | Kobayashi et al. | |
| 5,114,781 A | 5/1992 | Morman | |
| 5,116,662 A | 5/1992 | Morman | |
| 5,118,762 A | 6/1992 | Chin | |
| 5,135,786 A | 8/1992 | Hayashi et al. | |
| 5,137,537 A | 8/1992 | Herron et al. | |
| 5,139,832 A | 8/1992 | Hayashi et al. | |
| 5,145,935 A | 9/1992 | Hayashi | |
| 5,147,345 A | 9/1992 | Young et al. | |
| 5,149,741 A | 9/1992 | Alper et al. | |
| 5,151,092 A | 9/1992 | Buell et al. | |
| 5,156,911 A | 10/1992 | Stewart | |
| 5,159,022 A | 10/1992 | Ikematu et al. | |
| 5,167,897 A | 12/1992 | Weber et al. | |
| 5,171,236 A | 12/1992 | Dreier et al. | |
| 5,188,627 A * | 2/1993 | Igaue et al. | 604/385.27 |
| 5,189,110 A | 2/1993 | Ikematu et al. | |
| 5,192,301 A | 3/1993 | Kamiya et al. | |
| 5,221,274 A | 6/1993 | Buell et al. | |
| 5,226,992 A | 7/1993 | Morman | |
| 5,234,999 A | 8/1993 | Tung et al. | |
| 5,242,436 A | 9/1993 | Weil et al. | |
| 5,246,433 A | 9/1993 | Hasse et al. | |
| 5,256,736 A | 10/1993 | Trepka et al. | |
| 5,260,345 A | 11/1993 | DesMarais et al. | |
| 5,269,755 A | 12/1993 | Bodicky | |
| 5,270,388 A | 12/1993 | Onishi et al. | |
| 5,296,184 A | 3/1994 | Wu | |
| 5,306,266 A | 4/1994 | Freeland | |
| 5,336,545 A | 8/1994 | Morman | |
| 5,342,338 A | 8/1994 | Roe | |
| 5,344,691 A * | 9/1994 | Hanschen et al. | 428/152 |
| 5,358,500 A | 10/1994 | Lavon et al. | |
| 5,358,783 A | 10/1994 | Diehl et al. | |
| 5,387,207 A | 2/1995 | Dyer et al. | |
| 5,387,450 A | 2/1995 | Stewart | |
| 5,397,316 A | 3/1995 | Lavon et al. | |
| 5,397,318 A | 3/1995 | Dreier | |
| 5,429,856 A * | 7/1995 | Krueger et al. | 604/370 |
| 5,439,459 A | 8/1995 | Tanji et al. | |
| 5,439,966 A | 8/1995 | Graham et al. | |
| 5,445,140 A | 8/1995 | Tovey | |
| 5,447,508 A * | 9/1995 | Numano et al. | 604/385.27 |
| 5,468,237 A | 11/1995 | Miller et al. | |
| 5,468,428 A | 11/1995 | Hanschen et al. | |
| 5,492,751 A | 2/1996 | Butt, Sr. et al. | |
| 5,499,978 A | 3/1996 | Buell et al. | |
| 5,501,679 A * | 3/1996 | Krueger et al. | 604/393 |
| 5,506,300 A | 4/1996 | Ward et al. | |
| 5,507,736 A | 4/1996 | Clear et al. | |
| 5,514,121 A | 5/1996 | Roe et al. | |
| 5,518,433 A | 5/1996 | Sneddon | |
| 5,518,801 A | 5/1996 | Chappell et al. | |
| 5,536,563 A | 7/1996 | Shah et al. | |
| 5,540,671 A | 7/1996 | Dreier | |
| 5,540,976 A | 7/1996 | Shawver et al. | |
| 5,545,690 A | 8/1996 | Trepka et al. | |
| 5,554,142 A | 9/1996 | Dreier et al. | |
| 5,554,145 A | 9/1996 | Roe et al. | |
| 5,569,234 A | 10/1996 | Buell et al. | |
| 5,571,096 A | 11/1996 | Dobrin et al. | |
| 5,580,411 A | 12/1996 | Nease et al. | |
| H1630 H | 1/1997 | Roe et al. | |
| 5,591,152 A | 1/1997 | Buell et al. | |
| 5,607,760 A | 3/1997 | Roe | |

| | | | |
|---|---|---|---|
| 5,609,587 A | 3/1997 | Roe | |
| 5,620,780 A | 4/1997 | Krueger et al. | |
| 5,625,222 A | 4/1997 | Yoneda et al. | |
| 5,634,913 A | 6/1997 | Stinger | |
| 5,635,191 A | 6/1997 | Roe et al. | |
| H1670 H | 7/1997 | Aziz et al. | |
| 5,643,588 A | 7/1997 | Roe et al. | |
| 5,648,167 A | 7/1997 | Peck | |
| 5,653,703 A | 8/1997 | Roe et al. | |
| 5,669,897 A | 9/1997 | Lavon et al. | |
| 5,691,034 A | 11/1997 | Krueger et al. | |
| 5,714,548 A | 2/1998 | Ma et al. | |
| 5,719,226 A | 2/1998 | Kegley | |
| H1732 H | 6/1998 | Johnson | |
| 5,762,641 A * | 6/1998 | Bewick-Sonntag et al. | 604/378 |
| 5,814,705 A | 9/1998 | Ward et al. | |
| 5,830,203 A | 11/1998 | Suzuki et al. | |
| 5,853,864 A | 12/1998 | Bunnelle | |
| 5,858,150 A | 1/1999 | Yarusso et al. | |
| 5,865,823 A | 2/1999 | Curro | |
| 5,889,118 A | 3/1999 | Delgado et al. | |
| 5,897,545 A | 4/1999 | Kline et al. | |
| 5,899,895 A * | 5/1999 | Robles et al. | 604/385.29 |
| 5,910,546 A | 6/1999 | Trepka et al. | |
| 5,916,206 A * | 6/1999 | Otsubo et al. | 604/385.27 |
| 5,934,470 A | 8/1999 | Bauer et al. | |
| 5,938,648 A | 8/1999 | Lavon et al. | |
| 5,941,864 A | 8/1999 | Roe | |
| 5,957,908 A | 9/1999 | Kline et al. | |
| 5,968,025 A | 10/1999 | Roe et al. | |
| 5,972,519 A | 10/1999 | Niessner et al. | |
| 5,977,430 A | 11/1999 | Roe et al. | |
| 5,997,520 A | 12/1999 | Ahr et al. | |
| 6,004,306 A | 12/1999 | Robles et al. | |
| 6,010,490 A | 1/2000 | Freeland et al. | |
| 6,013,063 A | 1/2000 | Roe et al. | |
| 6,025,071 A | 2/2000 | Cameron et al. | |
| 6,031,053 A | 2/2000 | Knoll et al. | |
| 6,063,838 A | 5/2000 | Patnode et al. | |
| 6,103,814 A | 8/2000 | Vandrongelen et al. | |
| 6,107,537 A | 8/2000 | Elder et al. | |
| 6,120,487 A | 9/2000 | Ashton | |
| 6,120,489 A | 9/2000 | Johnson et al. | |
| 6,120,866 A | 9/2000 | Arakawa et al. | |
| 6,140,433 A | 10/2000 | Zhang et al. | |
| 6,149,637 A | 11/2000 | Allen et al. | |
| 6,156,842 A | 12/2000 | Hoenig et al. | |
| 6,168,584 B1 | 1/2001 | Allen et al. | |
| 6,177,517 B1 | 1/2001 | Güntherberg et al. | |
| 6,179,820 B1 * | 1/2001 | Fernfors | 604/385.27 |
| 6,184,285 B1 | 2/2001 | Goodman et al. | |
| 6,187,696 B1 | 2/2001 | Lim et al. | |
| 6,190,768 B1 | 2/2001 | Turley et al. | |
| 6,193,701 B1 * | 2/2001 | Van Gompel et al. | 604/385.01 |
| 6,194,073 B1 | 2/2001 | Li et al. | |
| 6,197,889 B1 | 3/2001 | Knoll et al. | |
| 6,211,272 B1 | 4/2001 | Hansen et al. | |
| 6,235,847 B1 | 5/2001 | Hoshi et al. | |
| 6,245,050 B1 | 6/2001 | Odorzynski et al. | |
| 6,265,484 B1 | 7/2001 | Trepka et al. | |
| 6,265,485 B1 | 7/2001 | Trepka et al. | |
| 6,274,666 B1 | 8/2001 | Dougherty | |
| 6,274,685 B2 | 8/2001 | Blok et al. | |
| 6,288,149 B1 | 9/2001 | Kroll | |
| 6,300,208 B1 | 10/2001 | Talwar et al. | |
| 6,310,154 B1 | 10/2001 | Babcock et al. | |
| 6,357,499 B1 | 3/2002 | Kralevich, Jr. et al. | |
| 6,369,160 B1 | 4/2002 | Knoll et al. | |
| 6,372,853 B1 | 4/2002 | Li et al. | |
| 6,383,431 B1 | 5/2002 | Dobrin et al. | |
| 6,391,935 B1 * | 5/2002 | Hager et al. | 521/170 |
| 6,418,848 B1 | 7/2002 | Fujimoto et al. | |
| 6,419,798 B1 | 7/2002 | Topolkaraev et al. | |
| 6,423,807 B1 | 7/2002 | Oi et al. | |
| 6,432,098 B1 | 8/2002 | Kline et al. | |
| 6,444,755 B1 | 9/2002 | Deporter et al. | |
| 6,455,627 B1 | 9/2002 | De Keyzer et al. | |
| 6,465,557 B1 | 10/2002 | De Keyzer et al. | |
| 6,476,288 B1 | 11/2002 | Vanrijswijck et al. | |
| 6,482,191 B1 | 11/2002 | Roe et al. | |
| 6,521,704 B1 | 2/2003 | Hubbard et al. | |
| 6,531,544 B1 | 3/2003 | Vaughan et al. | |
| 6,533,987 B2 | 3/2003 | Topolkaraev et al. | |
| 6,565,549 B1 | 5/2003 | Allen et al. | |
| 6,571,704 B2 | 6/2003 | Fujimoto et al. | |
| 6,579,940 B1 | 6/2003 | Dove | |
| 6,592,995 B2 | 7/2003 | Topolkaraev et al. | |
| 6,593,430 B1 | 7/2003 | Knoll et al. | |
| 6,598,637 B2 | 7/2003 | Lechtenböhmer et al. | |
| 6,626,879 B1 | 9/2003 | Ashton et al. | |
| 6,627,673 B2 | 9/2003 | Topolkaraev et al. | |
| 6,635,041 B1 * | 10/2003 | Popp et al. | 604/385.25 |
| 6,648,869 B1 | 11/2003 | Gillies et al. | |
| 6,653,363 B1 * | 11/2003 | Tursi et al. | 521/174 |
| 6,657,000 B1 | 12/2003 | De Keyzer et al. | |
| 6,664,309 B2 | 12/2003 | Svenningsen et al. | |
| 6,664,436 B2 | 12/2003 | Topolkaraev et al. | |
| 6,673,857 B1 | 1/2004 | Knoll et al. | |
| H2100 H | 4/2004 | Hansen et al. | |
| 6,722,910 B2 | 4/2004 | Kajinuma | |
| 6,746,433 B1 | 6/2004 | Shimoe et al. | |
| 6,759,454 B2 | 7/2004 | Stephens et al. | |
| 6,759,481 B2 | 7/2004 | Tong | |
| 6,790,911 B2 | 9/2004 | Perevosnik et al. | |
| 6,818,093 B1 | 11/2004 | Taal et al. | |
| 6,827,806 B2 | 12/2004 | Uitenbroek et al. | |
| 6,844,383 B2 | 1/2005 | Hoshi et al. | |
| 6,887,916 B2 | 5/2005 | Zhou et al. | |
| 6,933,421 B2 | 8/2005 | Topolkaraev et al. | |
| 6,939,906 B2 | 9/2005 | Hoshi et al. | |
| 6,946,172 B2 | 9/2005 | Munn et al. | |
| 6,967,178 B2 | 11/2005 | Zhou et al. | |
| 6,969,441 B2 | 11/2005 | Welch et al. | |
| 6,978,486 B2 | 12/2005 | Zhou et al. | |
| 7,015,155 B2 | 3/2006 | Zhou et al. | |
| 7,056,411 B2 | 6/2006 | Desai et al. | |
| 7,074,484 B2 | 7/2006 | Topolkaraev et al. | |
| 7,087,287 B2 | 8/2006 | Curro et al. | |
| 7,223,261 B2 | 5/2007 | Müeller et al. | |
| 7,316,840 B2 | 1/2008 | Neculescz et al. | |
| 7,316,842 B2 | 1/2008 | Zhou et al. | |
| 7,331,946 B2 | 2/2008 | Shimada et al. | |
| 7,717,893 B2 * | 5/2010 | Hird et al. | 604/385.01 |
| 7,905,872 B2 * | 3/2011 | McKiernan et al. | 604/385.21 |
| 8,029,488 B2 * | 10/2011 | Ashton et al. | 604/385.24 |
| 8,182,456 B2 * | 5/2012 | Autran et al. | 604/385.22 |
| 8,323,257 B2 * | 12/2012 | Melik et al. | 604/385.27 |
| 2001/0004689 A1 | 6/2001 | Otsubo | |
| 2002/0056384 A1 | 5/2002 | Fujimoto et al. | |
| 2002/0096072 A1 | 7/2002 | Fujimoto et al. | |
| 2002/0115744 A1 | 8/2002 | Svenningsen et al. | |
| 2002/0115772 A1 | 8/2002 | Topolkaraev et al. | |
| 2002/0115977 A1 | 8/2002 | Topolkaraev et al. | |
| 2002/0143313 A1 * | 10/2002 | Tsuji et al. | 604/385.03 |
| 2002/0147273 A1 | 10/2002 | Patel et al. | |
| 2002/0165516 A1 * | 11/2002 | Datta et al. | 604/385.16 |
| 2003/0088228 A1 * | 5/2003 | Desai et al. | 604/385.24 |
| 2003/0091807 A1 | 5/2003 | Desai et al. | |
| 2003/0111166 A1 | 6/2003 | Uitenbroek et al. | |
| 2003/0120240 A1 | 6/2003 | Buell et al. | |
| 2003/0233082 A1 | 12/2003 | Kline et al. | |
| 2004/0005832 A1 | 1/2004 | Zhou et al. | |
| 2004/0005834 A1 | 1/2004 | Zhou et al. | |
| 2004/0005835 A1 | 1/2004 | Zhou et al. | |
| 2004/0006324 A1 | 1/2004 | Zhou et al. | |
| 2004/0013852 A1 | 1/2004 | Curro et al. | |
| 2004/0092900 A1 | 5/2004 | Hoffman et al. | |
| 2004/0092902 A1 | 5/2004 | Hoffman | |
| 2004/0123938 A1 | 7/2004 | Zhou et al. | |
| 2004/0127881 A1 | 7/2004 | Stevens et al. | |
| 2004/0162536 A1 | 8/2004 | Becker et al. | |
| 2004/0162538 A1 | 8/2004 | Mueller | |
| 2004/0167486 A1 | 8/2004 | Busam et al. | |
| 2004/0181200 A1 * | 9/2004 | Desai et al. | 604/385.16 |
| 2004/0182499 A1 | 9/2004 | Zhou et al. | |
| 2004/0193134 A1 | 9/2004 | Mueller et al. | |
| 2004/0195137 A1 | 10/2004 | Otsubo | |
| 2004/0222553 A1 | 11/2004 | Desai et al. | |

| | | | |
|---|---|---|---|
| 2005/0095942 A1 | 5/2005 | Mueller | |
| 2005/0096416 A1 | 5/2005 | Zhou et al. | |
| 2005/0170729 A1 | 8/2005 | Stadelman et al. | |
| 2005/0171499 A1 | 8/2005 | Nigam et al. | |
| 2005/0177123 A1 | 8/2005 | Catalan | |
| 2005/0211368 A1* | 9/2005 | McGuire et al. | 156/230 |
| 2005/0215963 A1* | 9/2005 | Autran et al. | 604/358 |
| 2005/0215972 A1* | 9/2005 | Roe et al. | 604/385.29 |
| 2005/0215973 A1* | 9/2005 | Roe et al. | 604/385.29 |
| 2005/0224000 A1* | 10/2005 | Holte | 119/28.5 |
| 2005/0256476 A1* | 11/2005 | Mirle et al. | 604/382 |
| 2005/0273071 A1* | 12/2005 | McKiernan et al. | 604/385.24 |
| 2005/0273072 A1* | 12/2005 | Hird et al. | 604/385.24 |
| 2005/0287892 A1* | 12/2005 | Fouse et al. | 442/59 |
| 2006/0003656 A1 | 1/2006 | Morman | |
| 2006/0004342 A1* | 1/2006 | Sawyer et al. | 604/385.22 |
| 2006/0058765 A1 | 3/2006 | Mueller | |
| 2006/0078042 A1 | 4/2006 | Lee | |
| 2006/0083900 A1* | 4/2006 | Ashraf | 428/182 |
| 2006/0155255 A1 | 7/2006 | McKiernan et al. | |
| 2006/0167434 A1* | 7/2006 | Ashton et al. | 604/392 |
| 2006/0264858 A1* | 11/2006 | Roe et al. | 604/361 |
| 2007/0037907 A9 | 2/2007 | Zhou et al. | |
| 2007/0088307 A1 | 4/2007 | Arizti | |
| 2007/0093771 A1 | 4/2007 | Arizti | |
| 2007/0191806 A1 | 8/2007 | Mueller | |
| 2007/0197993 A1 | 8/2007 | Arizti | |
| 2007/0197994 A1 | 8/2007 | Arizti | |
| 2008/0033388 A1 | 2/2008 | Mueller | |
| 2008/0108963 A1 | 5/2008 | Ashton et al. | |
| 2008/0195070 A1 | 8/2008 | Ponomarenko | |

FOREIGN PATENT DOCUMENTS

| | | |
|---|---|---|
| EP | 119 827 A2 | 9/1984 |
| EP | 0 316 671 | 11/1988 |
| EP | 0 433 951 B1 | 6/1991 |
| EP | 0 591 647 B1 | 4/1994 |
| EP | 0 597 331 A1 | 5/1994 |
| EP | 451 919 B1 | 2/1995 |
| EP | 0 650 714 A1 | 5/1995 |
| EP | 0 703 068 B1 | 3/1996 |
| EP | 0 847 738 A1 | 6/1998 |
| EP | 1 013 291 A1 | 6/2000 |
| EP | 1351815 | 2/2005 |
| EP | 1226018 | 10/2005 |
| GB | 2 297 473 A | 8/1995 |
| GB | 2 287 888 A | 10/1995 |
| GB | 2 328 158 A | 2/1999 |
| GB | 2 329 842 A | 4/1999 |
| JP | 62241944 A | 10/1987 |
| JP | 63238153 A | 10/1988 |
| JP | 3160083 A | 7/1991 |
| JP | 3160084 A | 7/1991 |
| JP | 3239738 A | 10/1991 |
| JP | 4153288 A | 5/1992 |
| JP | 7157738 A | 6/1995 |
| JP | 8060120 A | 3/1996 |
| JP | 8060121 A | 3/1996 |
| JP | 8277382 A | 10/1996 |
| JP | 8281764 A | 10/1996 |
| JP | 9291265 A | 11/1997 |
| JP | 9302319 A | 11/1997 |
| JP | 2000-282006 | 5/1999 |
| JP | 11279521 A | 10/1999 |
| JP | 2001040302 A | 2/2001 |
| JP | 2001279212 A | 10/2001 |
| JP | 2001293789 | 10/2001 |
| JP | 2001293789 A | 10/2001 |
| WO | WO 94/14395 A1 | 7/1994 |
| WO | WO 95/16746 A1 | 6/1995 |
| WO | WO 96/23823 | 1/1996 |
| WO | WO 96/11236 A1 | 4/1996 |
| WO | WO 98/08476 | 3/1998 |
| WO | WO 99/13016 A1 | 3/1999 |
| WO | WO 00/12645 A1 | 3/2000 |
| WO | WO 00/30581 A | 6/2000 |
| WO | WO 00/69834 | 11/2000 |
| WO | WO 00/22061 A8 | 9/2001 |
| WO | WO 01/87589 A | 11/2001 |
| WO | WO 02/083786 A1 | 10/2002 |
| WO | WO 03/047488 A | 6/2003 |
| WO | WO 03/082571 A | 10/2003 |
| WO | WO 2006/074481 | 7/2006 |

OTHER PUBLICATIONS

Pritchard, Barbara, Introducing the pressure support surfaces from Kaymed, Kaymed Product Focus, British Journal of Nursing, 2001, vol. 10, No. 21, pp. 1427-1431.*

Polymer Handbook, Wiley Interscience, Section VII, 3$^{rd}$ Edition, pp. 519-559, USA.

U.S. Appl. No. 11/144,508, filed Jun. 3, 2005, Office Action dated May 18, 2007.

U.S. Appl. No. 11/144,508, filed Jun. 3, 2005, Office Action dated Jul. 16, 2008.

U.S. Appl. No. 11/144,508, filed Jun. 3, 2005, Interview Summary dated Sep. 25, 2008.

U.S. Appl. No. 11/144,497, filed Jun. 3, 2005, Office Action dated May 1, 2008.

U.S. Appl. No. 11/340,803, filed Jan. 26, 2006, Office Action dated Jun. 18, 2008.

Ziabicki, *Fundamentals of Fibre Formation*, John Wiley & Sons, New York (1976), Chapter 6.

J.H. Briston, *Plastic Films*, 2$^{nd}$ Edition, Longman Inc., New York (1983), pp. 83-85.

I.M. Ward, *Mechanical Properties of Solid Polymers*, Wiley-Interscience, New York (1971), p. 278.

U.S. Appl. No. 11/144,508, filed Jun. 3, 2005, Herd et al., Office Action dated Mar. 16, 2009.

U.S. Appl. No. 11/144,508, filed Jun. 3, 2005, Herd et al., Office Action dated Jul. 16, 2008.

U.S. Appl. No. 11/144,508, filed Jun. 3, 2005, Herd et al., Office Action dated May 18, 2007.

U.S. Appl. No. 11/340,803, filed Jan. 26, 2006, Ashton et al., Office Action dated Apr. 7, 2009.

U.S. Appl. No. 11/340,803, filed Jan. 26, 2006, Ashton et al., Office Action dated Dec. 16, 2008.

U.S. Appl. No. 11/340,803, filed Jan. 26, 2006, Ashton et al., Office Action dated Jun. 18, 2008.

U.S. Appl. No. 11/144,497, filed Jun. 3, 2005, McKiernan et al., Office Action dated Jan. 22, 2009.

U.S. Appl. No. 11/144,497, filed Jun. 3, 2005, McKiernan et al., Office Action dated May 1, 2008.

International Search Report.

* cited by examiner

ABSORBENT ARTICLES WITH STRETCH ZONES COMPRISING SLOW RECOVERY ELASTIC MATERIALS

CROSS REFERENCE TO RELATED APPLICATION

This application claims the benefit of U.S. Provisional Application No. 60/643,920, filed Jan. 10, 2005.

FIELD OF THE INVENTION

This invention is directed to absorbent articles such as diapers, training pants, adult incontinence articles, feminine hygiene articles, and the like comprising a slow recovery elastomer.

BACKGROUND OF THE INVENTION

Disposable absorbent articles, such as diapers, training pants, and incontinence articles typically include stretchable materials in waist and cuff regions to provide a snug fit and a good seal of the article. Absorbent articles generally include stretchable materials in the side portions for easy application and removal of the article and for sustained fit of the article. Stretchable materials have also been used in the ear portions of disposable diapers for adjustable fit of the article. Stretchable materials may allow the absorbent product to accommodate a range of different sized wearers.

Stretchable materials found in current absorbent products often comprise an elastic member which is generally disposed on or joined to a substrate. Conventional or traditional elastomeric compositions provide the requisite unload forces upon elongation, which may enable the stretchable materials to function effectively to provide a snug fit and/or good seal. However, these elastomeric compositions tend to retract relatively rapidly when released from a stretched state. This rapid retraction complicates the application of the absorbent article.

During application, a diaper generally may be stretched and elongated longitudinally and/or laterally from its initial substantially compacted and untensioned state. Upon release of the elongating tension, the diaper often contracts, constricts, and/or folds before it can be successfully applied to or adjusted on a wearer. In traditional fastenable diapers, the diaper generally is stretched and elongated longitudinally for application onto a wearer. However, if a continuous force is not maintained, the diaper will quickly retract. Generally, a caregiver may need to apply a continuous elongating force to the diaper while positioning the diaper onto the wearer and while tending to the wearer who may not be cooperating (e.g., crying, fussing, moving, resisting, etc.) in the diapering process. Similarly, in pant-type articles, the waist region generally must be stretched and elongated to enlarge the waist opening from an initial substantially constricted and untensioned state. The waist often requires a continuous force to be applied during the application process, generally by a caregiver or wearer, to counteract the rapid retraction of the waist opening that would be experienced without application of the force. Leg openings in pants-type articles also tend to retract quickly and/or constrict the leg with force during application, increasing the difficulty of pulling the article up to the desired location on the wearer's upper thigh.

Certain materials often border on or to some degree approach exhibiting elastic characteristics. Furthermore, such materials may recover to their original dimensions relatively slowly after a deforming force has been removed. However, such materials are generally unable to provide the necessary unload forces to perform desirable functions such as providing a snug fit and/or a good seal. If the stretchable material is unable to provide the desired unload forces, the absorbent article may fail to maintain the proper fit and/or waste containment during normal wearing conditions. Failure in either fit or containment is highly undesirable in absorbent article such as diapers.

In light of these problems with current stretchable materials, a need exists for an absorbent article comprising an elastomeric composition that retract slowly upon being released from a stretched state, so as to facilitate application and positioning of the product correctly onto the wearer, and that also exhibit requisite unload forces, so as to provide the desired fit and/or containment of the absorbent article.

SUMMARY OF THE INVENTION

The present invention is directed to an absorbent article having a stretch zone comprising a slow recovery elastomer wherein said slow recovery elastomer exhibits a normalized unload force of greater than about 0.04 N/mm$^2$ at 37° C.; and said slow recovery elastomer exhibits at least about 20% post elongation strain at 22° C. after 15 seconds of recovery from a 400% strain. Further, the slow recovery elastomer may exhibit a post elongation strain of at least about 40% after 60 seconds of recovery at 22° C. or a post elongation strain from about 100% to about 150% after 15 seconds of recovery at 22° C. And, the absorbent article may comprise a curvilinear stretch zone, at least a portion of the curvilinear stretch zone having a radius of curvature between about 1 mm and about 1 m. The stretch zone may have a width dimension of at least about 0.2 mm and a thickness dimension of at least about 0.1 mm. Further, the absorbent article may comprise a first plurality of stretch zones that comprise a first slow recovery elastomer and a second plurality of stretch zones that comprise a second slow recovery elastomer, wherein the first slow recovery elastomer and second slow recovery elastomer differ in one or both of the normalized unload force at 37° C. and the post elongation strain at 22° C. after 15 seconds of recovery from a 400% strain.

The present invention further relates to an absorbent article having a longitudinal centerline and a lateral centerline and the article further comprises at least one feature selected from the group consisting of: a liquid permeable topsheet, a liquid impermeable backsheet, an absorbent core, an ear, a side panel, a waist feature, a fastener component, and combinations thereof; wherein said feature comprises at least a part of the stretch zone.

The present invention is further directed to a package comprising one or more absorbent articles having a longitudinal centerline and a lateral centerline and the article further comprises at least one feature selected from the group consisting of: a liquid permeable topsheet, a liquid impermeable backsheet, an absorbent core, an ear, a side panel, a waist feature, a fastener component, and combinations thereof; wherein said feature comprises at least a part of the stretch zone and overwrap binding the one or more absorbent articles as an entity.

BRIEF DESCRIPTION OF THE DRAWINGS

While the specification concludes with claims particularly pointing out and distinctly claiming the subject matter that is regarded as the present invention, it is believed that the invention will be more fully understood from the following description taken in conjunction with the accompanying drawings.

DETAILED DESCRIPTION OF THE PRESENT INVENTIONS

Definitions

Figure 1:
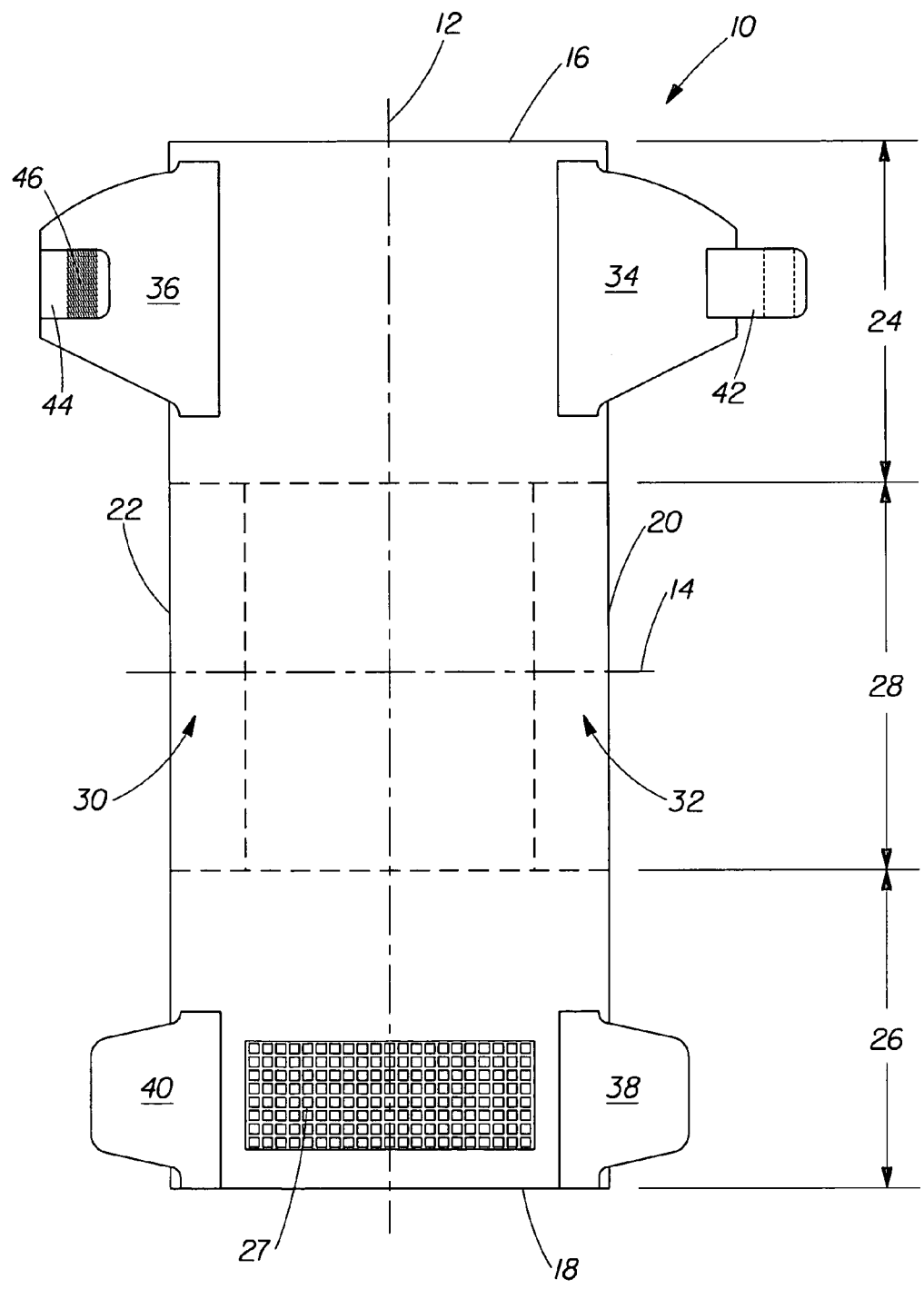
FIG. 1 is a plan view of a diaper in accordance with the invention.

As used herein, the term "absorbent article" or "article" refers to a wearable device that absorbs and/or contains liquid and, more specifically, refers to a device that is placed against or in proximity to the body of the wearer to absorb and contain the various exudates discharged from the body. Suitable examples include diapers, training pants, refastenable pants, pull-on garments, adult incontinence products and feminine care products such as sanitary napkins. Furthermore, "absorbent article" includes "disposable absorbent article" which is intended to be discarded and not laundered or otherwise restored after no more than ten uses, preferably after no more than five uses, and most preferably after a single use (although certain components may be recycled, reused, or composted).

As used herein, the term "diaper" refers to an absorbent article generally worn by infants and incontinent persons about the lower torso.

As used herein, the term "disposed" is used to mean that an element(s) is formed (joined and positioned) in a particular place or position as a unitary structure with other elements or as a separate element joined to another element.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

The term "substrate" as used herein refers to any material, including a film, an apertured film, a nonwoven web, a woven web, a foam or a combination thereof, or a cellulosic material including wood pulp, derivatized or modified cellulosic materials, and the like, having a single layer or multiple layers.

The term "nonwoven" as used herein refers to a fabric made from continuous filaments and/or discontinuous fibers. Nonwoven fabrics include those made by carding staple fibers, airlaying or wet laying staple fibers and via extrusion processes such as spunbonding and melt blowing. The nonwoven fabric can comprise one or more nonwoven layers, wherein each layer can include continuous filaments or discontinuous fibers. Nonwovens may also comprise bi-component fibers, which can have shell/core, side-by-side, or other known fiber structures.

As used herein, the terms "elastic" and "elastomeric" refer to a material that generally is able to extend to a strain of at least 50% without breaking or rupturing, and is able to recover substantially to its original dimensions after the deforming force has been removed. Ideally, the material will elongate to a strain of at least 100% without breaking or rupturing, and is able to recover substantially to at least about 120% of its original dimensions fifteen minutes after the deforming force has been removed while at 32° C.

The term "inelastic" refers herein to any material that does not fall within the definition of "elastic" above.

"Longitudinal" is a direction running parallel to the maximum linear dimension of the article and includes directions within ±45° of the longitudinal direction. The "lateral" or "transverse" direction is orthogonal to the longitudinal direction. The "Z-direction" is orthogonal to both the longitudinal and transverse directions. The "x-y plane" refers to the plane congruent with the longitudinal and transverse directions.

As used herein, the term "impermeable" generally refers to articles and/or elements that are not penetrative by fluid through the entire Z-directional thickness of the article under pressure of 0.14 lb/in$^2$ or less. Preferably, the impermeable article or element is not penetrative by fluid under pressures of 0.5 lb/in$^2$ or less. More preferably, the impermeable article or element is not penetrative by fluid under pressures of 1.0 lb/in$^2$ or less. The test method for determining impermeability conforms to EDANA 120.1-18 or INDA IST 80.6, as described in U.S. patent application Ser. No. 10/844,182 filed May 12, 2004.

As used herein, the term "line of force" describes the pathway through a web material or structure comprising such web material that is substantially parallel to its surface, that connects two points, zones, or features in the material, and that carries most of the tension when tension is imposed between those two points, zones, or features. The term also applies to pluralities of pathways of close enough proximity, properties, and direction that they effectively behave as a single pathway. The shape, width, and stress/strain behavior of the pathway can be controlled by modifying the stress/strain properties of the material in the desired location and direction of the pathway to produce a higher effective elastic modulus in the pathway compared to areas adjacent to the pathway. The proportion of the tension carried by the pathway depends on the difference in effective modulus between the pathway and the adjacent material. It should be understood that a line of force may be defined by any of the stretch element geometries disclosed herein.

As used herein, "relaxed" or "relaxed state" means the state that no biasing forces are applied to the article (other than naturally occurring forces such as gravity), when the article is laid on a horizontal surface.

As used herein, the terms "extendible" and "extensible" (e.g. extensibility of the elastomer) mean that the width or length of the item in the relaxed position can be extended or increased.

As used herein, "elasticated" or "elasticized" means that the component comprises at least a portion made of elastic material.

As used herein, the terms "elastic", "elastomer" and "elastomeric" refer to a material which generally is able to extend to a strain of at least 50% without breaking or rupturing, and is able to recover substantially to its original dimensions after the deforming force has been removed.

As used herein, the term "copolymer" refers to a polymer synthesized from two or more monomers with different chemical structures.

As used herein, the terms "temperature responsive" and "temperature responsiveness" refer to material that exhibits less post elongation strain after a specified amount of time at some higher temperature than the material exhibits at some lower temperature.

As used herein, the term "slow recovery elastomer" refers to elastomeric compositions that exhibit at least about 20% post elongation strain at 22° C. after 15 seconds of recovery as measured by the Post Elongation Recovery Test and exhibit a normalized unload force at 37° C. of greater than about 0.04 N/mm$^2$ as measured by the Two Cycle Hysteresis Test.

As used herein, the term "traditional elastomer" refers to elastomeric compositions that exhibit minimal post elongation strain at 22° C. after 15 seconds of recovery as measured by the Post Elongation Recovery Test. Traditional elastomers exhibit less than about 20% post elongation strain at 22° C. after 15 seconds of recovery as measured by the Post Elongation Recovery Test.

As used herein, the term "stretch zone" means a portion of an absorbent article having elastic stretch properties. A stretch zone may extend throughout an entire region or feature of the article, extend across multiple regions or features, or comprise merely a portion of one or more regions or features of the article. A region or feature may also comprise an array of individual stretch zones. The elastic stretch properties of the stretch zone may be imparted by an elastomeric material such as a recovery elastomer as described herein.

As used herein, the term "linear stretch zone" refers to a stretch zone bounded by one or more edges wherein the edge having longest dimension is substantially linear. A "linear stretch zone" should not be read as limited to exhibiting only linear elastic characteristics.

As used herein, the term "curvilinear stretch zone" refers to a stretch zone bounded by one or more edges wherein the edge having longest dimension is curvilinear.

As used herein, the term "array" means a set of more than one stretch zones. Generally, the stretch zones within an array share a common attribute such as, but not limited to, size, shape, orientation, and/or composition.

The present invention relates to an absorbent article comprising at least one stretch zones wherein the stretch zone comprises a slow recovery elastomer. The article may also include one or more features such as, but not limited to, a liquid permeable topsheet, a liquid impermeable backsheet, an absorbent core, an ear, a side panel, a waist feature, a fastener component, a leg cuff, a gasketing cuff, a barrier cuff, and combinations thereof. The aforementioned features may comprise at least a portion of a stretch zones so as to provide stretch character to the feature.

In some embodiments the stretch zone may have a geometric pattern (i.e., shape and orientation) so as to provide such elastic resistance in a manner that enhances the performance of the feature. In embodiments where an elastomer provides the stretch properties to the stretch zone, the geometric pattern of a stretch zone, generally, may be defined by the geometry of the elastomer. For example, if the elastomer is in a form such as a band, strand, film; the stretch zone may be defined by the geometry of the band, strand, or film. For example, if the elastomer was formed by deposition, printing, or the like onto a substrate; the stretch zone may be defined by the geometry of the pattern of deposition or printing. The pattern may allow the stretch zone to more efficiently carry anchoring loads and tensile forces induced by application of the article to the wearer and/or accommodate movement of the wearer, and/or the weight of the article or waste contents of the article than a typical non-patterned design.

In some embodiments, the stretch zone comprises an elastomer that may be unjoined or completely to partially joined to a substrate. Elastomers may be attached to the substrate by any number of bonding methods known to those skilled in the art, including adhesive bonding, thermal bonding, pressure bonding, ultrasonic bonding, and the like. Elastomers may be placed onto a substrate via known deposition techniques such as printing, extrusion coating, roll coating, and the like. For example, the elastomer may be applied to a substrate by letterpress application as described in U.S. Application No. 60/557,272 entitled "Letterpress Application of Elastomeric Compositions," filed on Mar. 26, 2004. The elastomer may be applied to a substrate by a print method such as, for example, gravure roll printing as described in U.S. application Ser. No. 10/966,759, entitled "Method For Producing a Corrugated Stretch Laminate," filed in the name of A. Ashraf on Oct. 15, 2004.

In some embodiments, an absorbent article may comprise stretch zones that are associated so as to provide an array thereof. Such an array may be disposed on only one region or feature of the absorbent article or may extend across two or more regions or features. The array can comprise intersecting or non-intersecting stretch zones. Also, the stretch zones in the array can either be parallel to one another or form a non-zero angle with respect to each other. An array of stretch zones comprising an elastomer may have open areas not covered by the elastomer. These open areas may comprise from about 0% to about 95% of the total surface area of the array. The open area depends on the specific requirements demanded of the array. As an alternative embodiment, any stretch zone described or depicted herein may be substituted with an array that comprises more than one stretch zones.

The slow recovery elastomers of the present invention exhibit unique elastic and recovery characteristics. The slow recovery elastomer exhibits a normalized unload force of greater than about 0.04 N/mm$^2$ at 37° C. as measured by the Two Cycle Hysteresis Test. Normalized unload forces less than about 0.04 N/mm$^2$ at 37° C. are believed to be insufficient for use as an elastomer within absorbent articles. Stretch zones within absorbent articles must exhibit sufficient unload forces to provide necessary functionality. For example, the stretch zones of a leg cuff within an absorbent article generally should provide sufficient unload forces to maintain the article in snug, close contact to the wearer's skin and prevent leakage. In certain embodiments, the slow recovery elastomer may exhibit a normalized unload force of greater than about 0.08 N/mm$^2$ at 37° C. In other embodiments, the slow recovery elastomer may exhibit a normalized unload force of greater than about 0.12 N/mm² at 37° C.

The slow recovery elastomers of the current invention may exhibit at least about 20% post elongation strain at 22° C. after 15 seconds of recovery, as measured by the Post Elongation Recovery Test. By way of contrast, traditional elastomers (i.e., elastomers commonly used in disposable absorbent articles such as Vector® styrenic block copolymers from Dexco Polymers L.P., Houston, Tex.) exhibit minimal post elongation strain at 22° C. after 15 seconds of recovery.

Qualitatively, traditional elastomers exhibit "snap back" (i.e., the elastomer contracts relatively quickly after being released from a stretched state). In the case of a traditional fastenable diaper comprising a traditional elastomer, upon application and release of a tensioning force to the diaper, the elastomer contracts quickly, causing the diaper to fold, thus making it difficult to position and apply the diaper successfully. In the case of a pant-type article, the waist region may comprise a traditional elastomer which, upon application and release of a tensioning force, may causing the pant to constrict, thus making it difficult to pull up and apply. While the slow recovery elastomers of the current invention may exhibit a post elongation strain of at least about 20% at 22° C. after 15 seconds of recovery, in certain embodiments, the slow recovery elastomer may exhibit at least about 50% post elongation strain after 15 seconds of recovery at 22° C. In other embodiments, at 22° C. the slow recovery elastomer may exhibits a post elongation strain from about 75% to about 150% after 15 seconds of recovery. However, a post elongation strain after 15 seconds of recovery may exceed about 150% at 22° C.

Furthermore, the slow recovery elastomers of the present invention may exhibit a specified post elongation strain at 22° C. after 30 seconds, 60 seconds, or three minutes of recovery. In certain embodiments, the slow recovery elastomer may exhibit at least about a 20% post elongation strain after 30 seconds of recovery at 22° C. In other embodiments, the slow recovery elastomer may exhibit at least about a 20% post elongation strain after 60 seconds of recovery at 22° C. Other suitable embodiments may have the slow recovery elastomer exhibiting at least about a 20% post elongation strain after 180 seconds of recovery at 22° C.

The slow recovery elastomer of the present invention may exist in a variety of forms. The slow recovery elastomer forms include, but are not limited to films, bands, strands, individualized fibers, or combinations thereof. Furthermore, the slow recovery elastomer may take any of the previous forms and be further combined with a traditional elastic not exhibiting the unique rate of recovery of the present invention (i.e., an elastic not exhibiting at least about 20% post elongation strain after 15 seconds of recovery at 22° C.). The slow recovery elastomer may be utilized in a variety of articles. However, the composition has particular benefit within absorbent articles, particularly disposable absorbent articles such as diapers and the like. The slow recovery elastomer may be used in place of or in addition to traditional elastomers commonly present in absorbent articles.

The slow recovery elastomer may exhibit temperature responsiveness. As defined above, a temperature responsive material is one that exhibits less post elongation strain after a specified amount of time at higher temperatures than at lower temperatures. In one embodiment, the slow recovery elastomer may exhibit temperature responsiveness by exhibiting a post elongation strain after 15 seconds at 32° C. that is at least 35% less than the post elongation strain after 15 seconds at 22° C. (i.e., [[% post elongation strain after 15 seconds of recovery at 22° C.]–[% post elongation strain after 15 seconds of recovery at 32° C.]]/[% post elongation strain after 15 seconds of recovery at 22° C.]×100). In other embodiments, at least a 50% reduction in post elongation strain may be exhibited. It is believed that a slow recovery elastomer exhibiting temperature responsiveness may further facilitate diaper application. When the diaper is applied at about room temperature (e.g., approximately 22° C.), the slow recovery elastomer may exhibit a relatively high degree of post elongation strain for a prescribed period. Upon application of the diaper, the diaper and slow recovery elastomer may rise in temperature due in part to the close proximity of the wearer's skin. As the temperature of the slow recovery elastomer increases and reaches about skin temperature (e.g., approximately 32° C.), a reduced post elongation strain may be exhibited. Temperature responsiveness allows for application of the diaper without "snap-back" while providing for increased recovery after application.

A number of elastomeric polymers can be used to prepare the slow recovery elastomer with the requisite normalized unload force and post elongation strain. Elastomeric polymers include, but are not limited to, homopolymers (e.g., crosslinked poly(isoprene)), block copolymers, random copolymers, alternating copolymers, and graft copolymers. Suitable elastomeric polymers comprise styrenic block copolymers, natural and synthetic rubbers, polyisoprene, neoprene, polyurethanes, silicone rubbers, hydrocarbon elastomers, ionomers, and the like.

In one embodiment, the elastomeric polymer may be a block copolymer. A number of block copolymers may be used to prepare the slow recovery elastomer including multi-block, tapered block and star block copolymers.

Generally, the block copolymers suitable for use in the slow recovery elastomer may exhibit both elastomeric and thermoplastic characteristics. In such block copolymers a hard block (or segment) may have a glass transition temperature (Tg) greater than about 25° C. or is crystalline or semicrystalline with a melting temperature (Tm) above about 25° C. Preferably, the hard block has a Tg greater than about 35° C. or is crystalline or semicrystalline with a Tm above about 35° C. The hard block portion is typically derived from vinyl monomers including vinyl arenes such as styrene and alphamethyl-styrene or combinations thereof.

Glass transition temperatures referred to herein with reference to elastomeric polymers and the slow recovery elastomer of the present invention are determined by tensile dynamic mechanical analysis performed in the linear elastic region of the material at a frequency of 1 Hz using a temperature ramp method. Suitably, film samples with a uniform thickness of about 0.3 mm or less may be used with a temperature ramp rate of about 1° C./min or slower. The tan δ peak temperature is taken as the Tg of the particular material or phase.

Crystalline melting temperatures referred to herein are determined by Differential Scanning Calorimetry using a temperature ramp rate of 10° C./min. The melting endotherm peak temperature is taken as the Tm of the particular crystalline region.

In these block copolymers, a soft block (or segment) generally may exhibit a sufficiently low glass transition temperature and/or melting temperature so as not to form glassy or crystalline regions at the use temperature of the copolymer. In one embodiment, the use temperature may be between about ambient room temperature and about body temperature. Such soft blocks are generally physically incompatible with the hard blocks and form separate regions, domains, or phases.

The soft block portion may be a polymer derived from conjugated aliphatic diene monomers. Typically, the soft block monomers contain fewer than about 6 carbon atoms.

Suitable diene monomers include butadiene, isoprene, and the like. Suitable soft block polymers include poly(butadiene) and poly(isoprene). Furthermore, it is envisioned that the soft block may be modified so as to tailor the Tg of the soft block. For example, a random copolymer of isoprene and styrene or a graft of styrene onto poly(isoprene) may be used. In such cases, lower amounts of the modifying resin may be used.

Suitable block copolymers for use in this invention may comprise at least one hard block (A) and at least one soft block (B). The block copolymers may have multiple blocks. In a preferred embodiment, the block copolymer may be an A-B-A triblock copolymer, an A-B-A-B tetrablock copolymer, or an A-B-A-B-A pentablock copolymer. Also, useful herein are triblock copolymers having endblocks A and A', wherein A and A' may be derived from different vinyl compounds. Also, useful in the present invention are block copolymers having more than one hard block and/or more than one soft block, wherein each hard block may be derived from the same or different monomers and each soft block may be derived from the same or different monomers.

It should be noted that where the copolymer contains residual olefinic double bonds, the copolymer may be partially or fully hydrogenated if desired. Saturation may often yield beneficial effects in the elastomeric properties of the copolymer.

The elastomeric polymer may be used in the slow recovery elastomer in an effective amount so as to achieve the desired normalized unload forces and post elongation strains. The slow recovery elastomer generally may comprise from about 20% to about 70%, preferably about 30% to about 65%, and most preferably about 45% to about 60% of the elastomeric polymer.

Preferred elastomeric polymers include styrene-olefin-styrene triblock copolymers such as styrene-butadiene-styrene (S-B-S), styrene-ethylene/butylene-styrene (S-EB-S), styrene-ethylene/propylene-styrene (S-EP-S), styrene-isoprene-styrene (S-I-S), hydrogenated polystyrene-isoprene/butadiene-styrene (S-IB-S), and mixtures thereof. The block copolymers may be employed alone or in a blend of block copolymers.

Particularly preferred block copolymers include styrene-butadiene-styrene (S-B-S) and styrene-isoprene-styrene (S-I-S) block copolymers. Such linear block copolymers of styrene-butadiene-styrene (S-B-S) and styrene-isoprene-styrene (S-I-S) are commercially available under the trade designation Vector® from Dexco Polymers L.P., Houston, Tex., and under the trade designation Kraton from Kraton Polymers, Houston, Tex.

Various modifying resins may be used in this slow recovery elastomer. Suitable modifying resins should preferably associate or phase mix with the soft blocks of the elastomeric polymer. Modifying resins should have a sufficiently high average molecular weight such that the glass transition temperature of the soft block is increased which results in an increase of post elongation strain at 22° C. after 15 seconds of recovery. While not intending to be bound by this theory, it is believed that the modifying resins raise the Tg of the soft phase to the point where molecular relaxation at the in-use temperature is slowed. This is evidenced by a relatively high post elongation strain.

The slow recovery elastomer may comprise the modifying resin in amounts from about 0% to about 60% by weight. Preferably, the composition comprises from about 20% to about 55% and even more preferably from about 40% to about 50% of the modifying resin.

Suitable modifying resins useful herein may have glass transition temperatures ranging from about 60° C. to about 180° C., more preferably from about 70° C. to about 150° C., and more preferably from about 90° C. to about 130° C. Glass transition temperatures referred to herein with reference to modifying resins are determined by Differential Scanning Calorimetry using a temperature ramp rate of 20° C./min and an average sample size of 3-5 mg. The Tg of the particular material was taken as the half-height of the transition during the second heating cycle.

Suitable modifying resins useful herein should preferably be soft block associating. A solubility parameter is useful in determining whether the modifying resin will phase mix with the soft block of the block copolymer. Generally, modifying resins are selected so that the solubility parameter of the modifying resin is similar to the solubility parameter of the soft block phase. Since common soft block phases have solubility parameters from about 7.0 $(cal/cm^3)^{1/2}$ to about 9.0 $(cal/cm^3)^{1/2}$, the modifying resins should have similar solubility parameters. For example in the case where the solubility parameter of the soft block phase is about 8 $(cal/cm^3)^{1/2}$, the solubility parameter of the modifying resin should be from about 7.5 $(cal/cm^3)^{1/2}$ to about 8.5 $(cal/cm^3)^{1/2}$. The solubility parameters of the modifying resins may also approximate the solubility of the hard block. However, as long as phase mixing of the modifying resin with the soft block exists, hard block phase mixing should not be read as limiting. A list of solubility parameters for common polymers or resins, along with methods for determining or approximating the solubility parameters can be found in the Polymer Handbook, Third Edition; Wiley Interscience; Section VII pages 519-559.

Modifying resins useful herein include, but are not limited to, unhydrogenated C5 hydrocarbon resins or C9 hydrocarbon resins, partially and fully hydrogenated C5 hydrocarbon resins or C9 hydrocarbon resins; cycloaliphatic resins; terpene resins; polystyrene and styrene oligomers; poly(t-butylstyrene) or oligomers thereof; rosin and rosin derivatives; coumarone indenes; polycyclopentadiene and oligomers thereof; polymethylstyrene or oligomers thereof; phenolic resins; indene polymers, oligomers and copolymers; acrylate and methacrylate oligomers, polymers, or copolymers; derivatives thereof; and combinations thereof. Preferably, the resin is selected from the group consisting of the oligomers, polymers and/or copolymers derived from: t-butylstyrene, cyclopentadiene, iso-bornyl methacrylate, methyl methacrylate, isobutyl methacrylate, indene, coumarone, vinylcyclohexane, methylstyrene, and 3,3,5-trimethylcyclohexyl methacrylate. Preferred modifying resins also include alicyclic terpenes, hydrocarbon resins, cycloaliphatic resins, polybeta-pinene, terpene phenolic resins, and combinations thereof. "C5 hydrocarbon resins" and "C9 hydrocarbon resins" are disclosed in U.S. Pat. No. 6,310,154.

In general, a variety of additives may be employed to yield a slow recovery elastomer with more favorable characteristics. For example, stabilizers, antioxidants, anti-blocking agents, and bacteriostats may be employed to prevent thermal, oxidative, and bio-chemical degradation of the slow recovery elastomer. Generally, the additive or additives may account for about 0.01% to about 60% of the total weight of the slow recovery elastomer. Preferably, the composition comprises from about 0.01% to about 25% and even more preferably from about 0.01% to about 10% by weight, of additives.

Various stabilizers and antioxidants are well known in the art and include high molecular weight hindered phenols (i.e., phenolic compounds with sterically bulky radicals in proximity to the hydroxyl group), multifunctional phenols (i.e., phenolic compounds with sulfur and phosphorous containing groups), phosphates such as tris-(p-nonylphenyl)-phosphite, hindered amines, and combinations thereof. Representative hindered phenols include t-butylhydroxyquinone; 1,3,5-trimethyl-2,4,6-tris(3-5-di-tert-butyl-4-hydroxybenzyl)benzene; pentaerythritol tetrakis-3(3,5-di-tert-butyl-4-hydroxyphenyl)propionate; n-octadecyl-3(3,5-ditert-butyl-4-hydroxyphenyl)propionate; 4,4'-methylenebis(4-methyl-6-tert butylphenol); 4,4'-thiobis(6-tert-butyl-o-cresol); 2,6-di-tert-butylphenol; 6-(4-hydroxyphenoxy)-2,4-bis(n-ocytlthio)-1,3,5-triazine; 2,4,6-tris(4-hydroxy-3,5-di-tert-butyl-phenoxy)-1,3,5-triazine; di-n-octadecyl-3,5-di-tert-butyl-4-ydroxybenzylphosphonate; 2-(n-octylthio)ethyl-3,5-di-tert-butyl-4-hydroxybenzoate; and sorbitol hexa-(3,3,5-di-tert-butyl-4-hydroxy-phenyl) propionate. Proprietary commercial stabilizers and/or antioxidants are available under a number of trade names including a variety of Wingstay®, Tinuvin® and Irganox® products.

Various bacteriostats are known in the art and may be included as additives within the slow recovery elastomer. Examples of suitable bacteriostats include benzoates, phenols, aldehydes, halogen containing compounds, nitrogen compounds, and metal-containing compounds such as mercurials, zinc compounds and tin compounds. A representative bacteriostat is 2,4,4'-trichloro-2'-hydroxy-diphenyl-ether which is available under the trade designation Irgasan PA from Ciba Specialty Chemical Corporation, Tarrytown, N.Y.

Other optional additives include thermoplastic polymers or thermoplastic polymer compositions which preferentially associate with the hard blocks or segments of the block copolymers. Without intending to be bound by theory, it is believed that these thermoplastic polymers become incorporated into the entangled three-dimensional network structure of the hard phase. This entangled network structure can provide improved tensile, elastic and stress relaxation properties of the elastomeric composition. Where the elastomeric polymer comprises a styrenic block copolymer, thermoplastic polymer additives such as polyphenylene oxide and vinylarene polymers derived from monomers including styrene, alpha-methyl styrene, para-methyl styrene, other alkyl styrene derivatives, vinyl toluene, and mixtures thereof, are useful in the present invention because they are generally considered to be chemically compatible with the styrenic hard blocks of the block copolymer.

Various viscosity modifiers, processing aids, slip agents or anti-block agents can be employed as additives to yield a slow recovery elastomer with, for example, improved handling characteristics or surface characteristics. Processing aids include processing oils, which are well known in the art and include synthetic and natural oils, naphthenic oils, paraffinic oils, olefin oligomers and low molecular weight polymers, vegetable oils, animal oils, and derivatives of such including hydrogenated versions. Processing oils also may incorporate combinations of such oils. A particularly preferred processing oil is mineral oil. Viscosity modifiers are also well known in the art. For example, petroleum derived waxes can be used to reduce the viscosity of the slow recovery elastomer in thermal processing. Suitable waxes include low number-average molecular weight (e.g., 600-6000) polyethylene; petroleum waxes such as paraffin wax and microcrystalline wax; atactic polypropylene; synthetic waxes made by polymerizing carbon monoxide and hydrogen such as Fischer-Tropsch wax; and polyolefin waxes.

Various colorants and fillers are known in the art and may be included as additives within the slow recovery elastomer. Colorants can include dyes and pigments such as titanium dioxide. Fillers may include such materials as talc and clay. Other additives may include dyes, UV absorbers, odor control agents, perfumes, fillers, dessicants, and the like.

Various anti-blocking agents are known in the art and may be included within the slow recovery elastomer composition. In certain embodiments, anti-blocking properties may be achieved by coextruding the slow recovery elastomer with a skin layer. The skin layer generally is a composition that is less elastomeric than the slow recovery elastomer composition. Coextrusion processes capable of forming such slow recovery elastomers with a skin layers are well known in the art.

Figure 2:
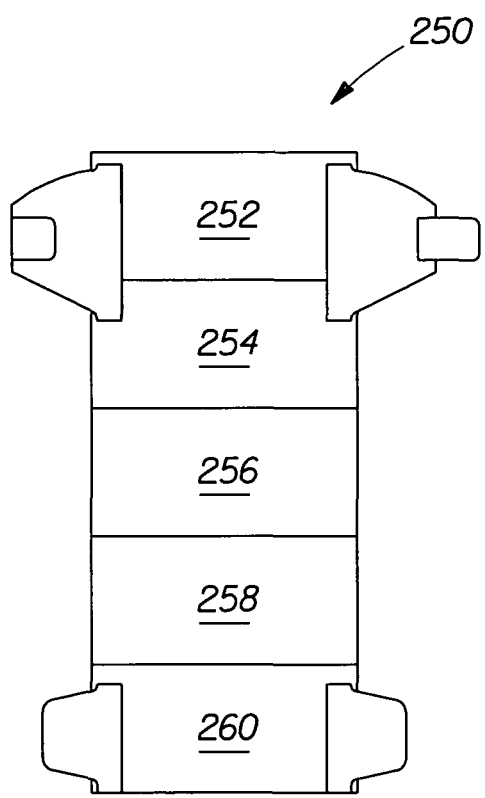
FIG. 2 is a perspective view showing a diaper chassis having a plurality of regions with one or more stretch zones or arrays according to the invention disposed thereon.

In the absorbent article embodiments that follow, the slow recovery elastomer of the present invention may be used wherever an elastic material is desired. Referring to FIG. 1, an absorbent article in the form of an open-style or taped diaper 10 is depicted. It should be understood that while FIGS. 1-2 depict a taped diaper, the present invention also contemplates other wearable absorbent articles, such as pants, catamenial products, and adult incontinence products, that encircle or enclose at least a portion of a wearer's anatomy or which are otherwise secured to a wearer. The diaper 10 has a longitudinal centerline 12 and a lateral centerline 14 as a frame of reference for this discussion. The diaper 10 may have a pair of opposed end edges 16 and 18, a pair of opposed side edges 20 and 22, a rear waist region 24, a front waist region 26, a crotch region 28 disposed intermediate the front and rear waist regions 26 and 24, respectively, and a pair of leg regions 30 and 32. The exact size of these various regions vary according to the size of the diaper 10, but generally speaking, the crotch region 28, front waist region 26 and rear waist region 24 represent equal one-third portions along the longitudinal centerline 12. The leg regions 30 and 32 generally represent the one-quarter areas across the width of the diaper 10 in the crotch region 28, and the crotch region 28 itself, represents the remaining center two-quarters or one-half the width of diaper 10.

The diaper 10 also may comprise one or more ears or side panels 34, 36, 38 and 40 disposed generally laterally outboard of the side edges 20, 22 in the front waist region 26 and/or rear waist region 24. In closable diaper 10 at least one fastener element 42 is disposed on one or more of side panels 34 and 36 and is adapted to be secured to at least a portion of the longitudinally opposing front side panels 38 and 40, or a portion of the outer surface of the front waist region 26 or a component thereof. An accompanying fastener element 44 is shown in a folded back configuration to expose the mechanical fasteners 46, which shown as hooks for a hook-and-loop fastening systems commercially available from 3M or Velcro Industries. The fastener element 44 may be capable of engaging loop material embodied in a landing zone 27 located on the outer surface of the diaper 10.

Any one or more of regions 24, 26, 28, 30, 32, 34, 36, 38, 40, 42 or 44 may comprise a stretch zone or array of stretch zones where at least one of said regions comprising a slow recovery elastomer. Any region of the diaper 10 may include a stretch zone or array of stretch zones.

Each stretch zone or array of stretch zones may have continuous or discontinuous properties in any direction wherein the varying properties include chemical composition, elasticity, extensibility, maximum elongation, other stress/strain properties, vectors or angles, basis weight, geometry, dimensions, 3-dimensional morphology, visual distinctiveness, and the like. A stretch zone having continuous properties generally comprise homogeneous constituents (e.g., material, treatment, composite, etc.). Alternatively, stretch zones may have non-homogeneous properties. An array may comprise stretch zones having the same or different properties. Suitable stretch zone shapes include straight or curved lines or bands, rectilinear shapes, curvilinear shapes, other regular or irregular geometric shapes, and combinations thereof which will be described in more detail hereinafter. Two stretch zones may be longitudinally separated or adjacent, laterally separated or adjacent, or the stretch zones may be at least partially overlapping in such arrays. Within an array, the individual stretch zones may vary in property, geometry, relative orientation, spacing, or elasticity or extensibility. For example, within an array, one stretch zone may comprise a slow recovery elastomer and another stretch zone may comprise a traditional elastomer (i.e., an elastomer that does not exhibit slow recovery characteristics; an elastomer that exhibits "snap-back"). Likewise, an array may comprise multiple stretch zones wherein each stretch zone comprises an elastomer having different post elongation strain, as measured by the Post Elongation Recovery Test, than an adjacent stretch zone. In certain embodiments, at least a portion of at least one stretch zone may be visually distinct. Stretch zones may be combined with other elastic, extensible, or inextensible materials, such as films, webs, strands, and the like to form laminates.

An exemplary diaper chassis comprising arrays of stretch zones is diaper chassis 250 shown in FIG. 2. The diaper chassis 250 may include a liquid impermeable backsheet and an outer cover made of a nonwoven material. Other chassis components may be included but are not depicted for purposes of clearly showing the array of stretch zones of the present invention. In one embodiment, an elastomer may be disposed on or joined to a standard liquid impermeable backsheet material in a way which creates different arrays of stretch zones in regions 252, 254, 256, 258 and 260, any of which may comprise a slow recovery elastomer as described herein. By way of example, an array in region 252 may comprise a first elastomer composition, while arrays in regions 254, 256, 258 and/or 260 may comprise a different composition or comprise the first composition disposed in a different configuration (thickness, width, pattern, etc.). In certain cases for purposes of enhancing fit on a wearer, the various stretch zone properties are symmetrical in that arrays in regions 252 and 260 have similar properties, arrays in regions 254 and 258 also have similar properties while an array in region 256 has a third type of elastic property. For example, arrays in regions 252, 254, 256, 258, 260, may comprise different elastomeric compositions with each composition exhibiting a unique post elongation strain as measured by the Post Elongation Recovery Test Method. It should be understood, however, that this is not necessary and the individual arrays in regions 252, 254, 256, 258 and 260 may vary individually and widely in terms of elastic properties, size, shape, and composition without deviating from the scope of the invention.

Reference is now made to FIGS. 3, 4 and 5A-B which show an absorbent article in the form a pant 370. The term "pant" or "pants," as used herein, refers to disposable garments having a waist opening defined by a continuous waist edge and leg openings designed for infant or adult wearers. A pant may be preformed by any suitable technique for joining together portions of the article to yield a waist opening defined by a continuous waist edge; such techniques include, but are not limited to, using refastenable and/or non-refastenable bonds (e.g., seam, weld, adhesive, cohesive bond, fastener, etc.). The joining together of portions of the article may occur anywhere along the circumference of the article to yield a waist opening defined by a continuous waist edge. While the term "pant" is used herein, pants are also commonly referred to as "closed diapers", "prefastened diapers", "pull-on diapers," "training pants," and "diaper-pants". Suitable pants are disclosed in U.S. Pat. No. 5,246,433, U.S. Pat. No. 5,569,234, U.S. Pat. No. 6,120,487, U.S. Pat. No. 6,120,489, U.S. Pat. No. 4,940,464, U.S. Pat. No. 5,092,861, U.S. Pat. No. 5,897, 545, U.S. Pat. No. 5,957,908, and U.S. patent application Ser. No. 10/171,249, entitled "Highly Flexible And Low Deformation Fastening Device", filed on Jun. 13, 2002.

Figure 3:
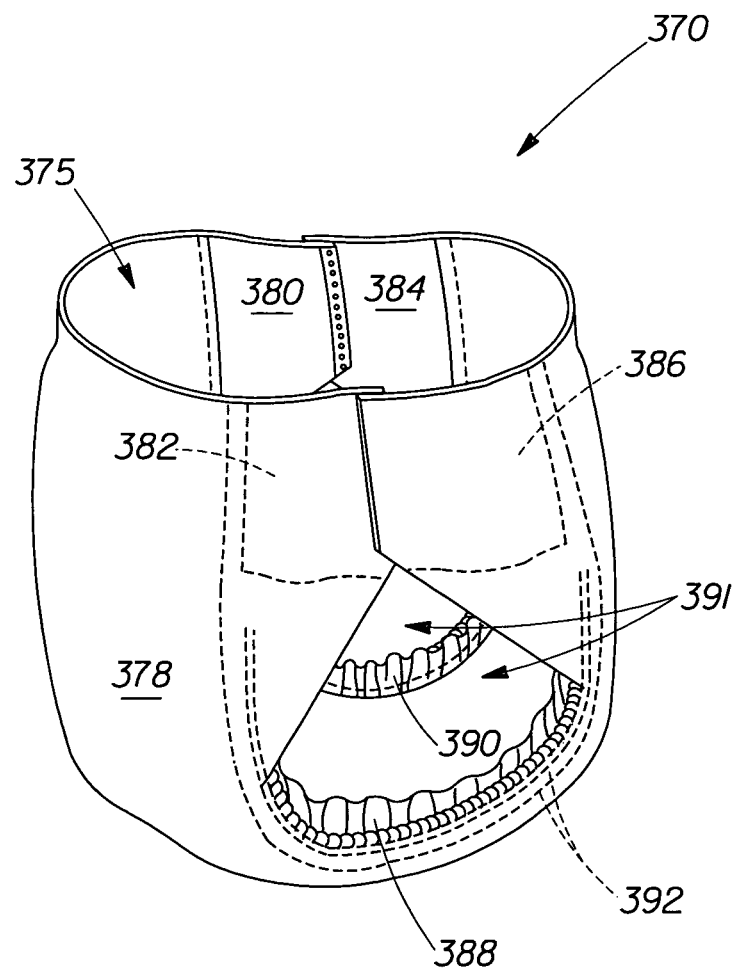
FIG. 3 is a perspective view of a pull-on diaper in accordance with the invention.
Figure 4:
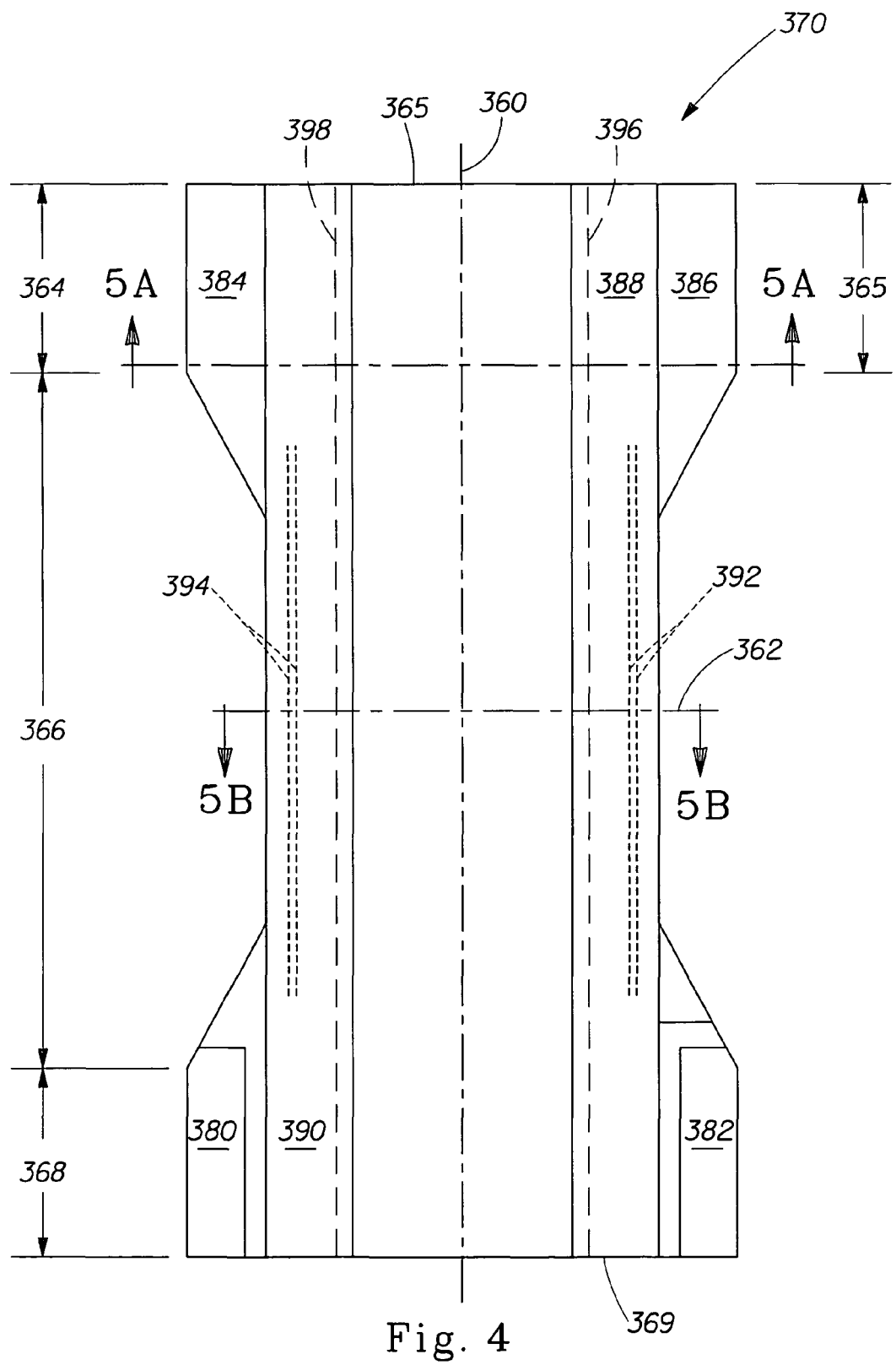
FIG. 4 is a plan view of the pull-on diaper of FIG. 2 in a flat-out, unseamed configuration.
Figure 5A:
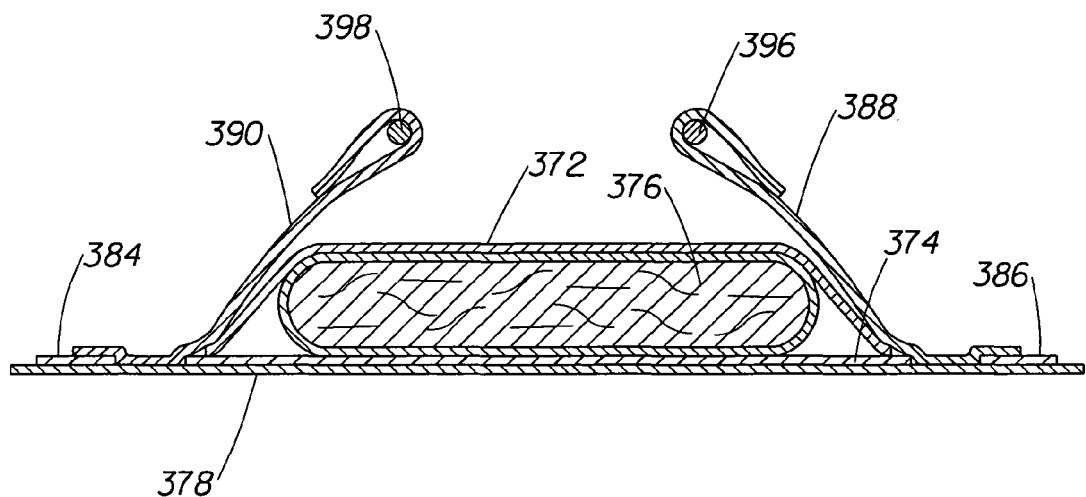
FIGS. 5A and 5B are cross-sectional views of the pull-on diaper shown in FIGS. 3 and 4.
Figure 5B:
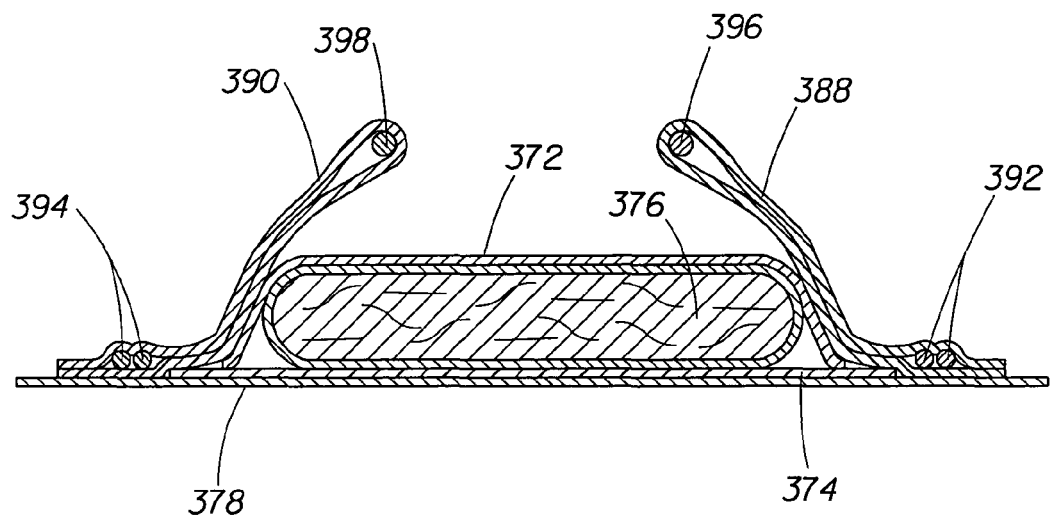

Pant 370 may include stretch zones to impart the desired elastic properties so that it may be donned easily and sustain better fit and comfort. Similar to the diaper 10, stretch zones may be included anywhere on the pant 370, and, as a result, any subsequent figure showing a stretch zone directed on a diaper is equally applicable to a similar stretch zone on a pant. FIG. 3 is a perspective view of pant 370 and FIG. 4 shows pant 370 in a plan view and in an unseamed configuration. As shown in FIG. 4, pant 370 has a longitudinal centerline 360, lateral centerline 362, a front waist region 364 (adjacent front waist edge 365), a crotch region 366 and a rear waist region 368 (adjacent rear waist edge 369). As can be seen most clearly in FIGS. 5A-B, pant 370 may include an absorbent assembly including liquid permeable topsheet 372, a liquid impermeable backsheet 374, and an absorbent core 376 disposed between the topsheet 372 and the backsheet 374. An outer cover 378 (typically comprising a nonwoven) may be disposed on the outer surface of the pant 370. Two pair of side panels 380, 382 and 384, 386 may be attached to the outer cover 378 in the front waist region 364 and the rear waist region 368, which in turn, may be attached to the backsheet 374 of the absorbent assembly so as to form a pair of leg openings 391 and a waist opening 375 for the wearer (375 and 391 are shown in FIG. 3). Desirably, stretch zones are disposed in at least one of the side panels 380, 382, 384 and/or 386. The stretch zones of pant 370 may also comprise the waist regions 364, 366, barrier leg cuffs 388 and 390. For example either or both of the leg elastics 392, 394, and/or the barrier leg cuff elastics 396, 398 could comprise an elastomeric composition, such as the slow recovery elastomer as described herein.

Figure 6A:
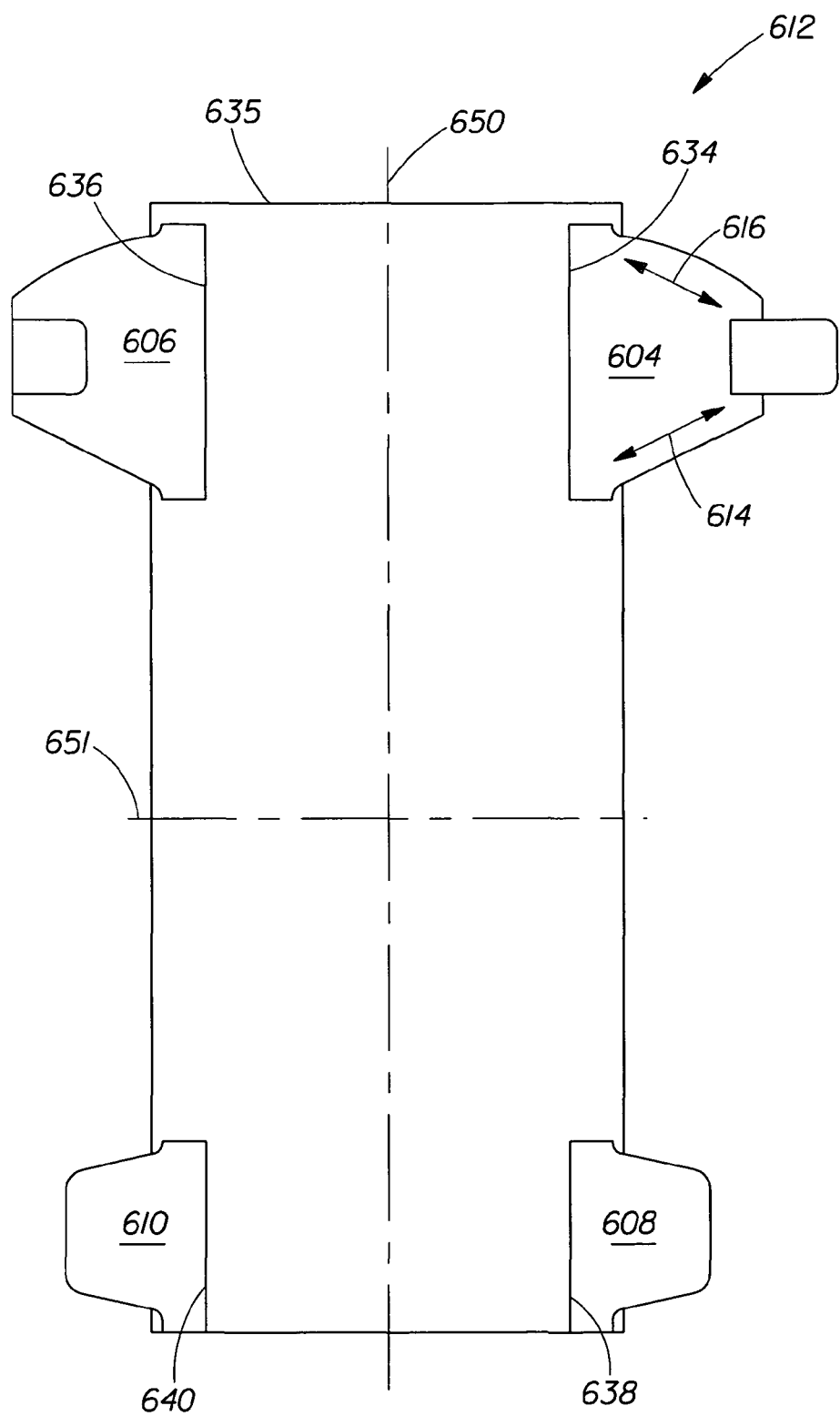
FIGS. 6A-I show diaper embodiments of the present invention in which the diaper ears have stretch zones in various designs.

Reference is made to FIG. 6A in which side panels 604, 606, 608, 610 are depicted for a closable open or taped diaper 612. As will be recognized, the side panels 604, 606, 608, 610 each have an inner edge 634, 636, 638 and 640 disposed at a predefined angle (usually parallel) with respect to longitudinal centerline 650. It should be understood that the side panels 604, 606, 608 and 610 (as well as side panels 605, 607, 609, 611, 613, 615, 617, and 629 as shown in FIGS. 6B-I) as described herein are interchangeable with any of the side panels or ears described in FIGS. 1-4 of the diapers 10 or 250 or pant 370. The stretch zone arrows 614, 616 are depicted to show exemplary force vectors desirable of typical side panels in diapers. The size of a given stretch zone in a region of the diaper 612 is dependent on the function of the stretch zone and the desired tension/extension vectors 614, 616 in that given region of the diaper 612. Each stretch zone may be smaller or larger than the region of the diaper 612 in which it is primarily disposed. A given stretch zone may also overlap other regions of the diaper 612.

Referring to FIGS. 6B-6I, various side panels 605, 607, 609, 611, 613, 615, 617, and 629 with varying stretch zones are depicted and may be used interchangeably with the side panel 604, 606, 608, and 610 of FIG. 6A or with the panels or ears described in FIGS. 1-4 of the diapers 10 or 250 or pant 370. FIGS. 6B-6I are merely exemplary to depict particular iterations of stretch zone configuration; however, other configurations are clearly within the realm of this invention.

As applicable to FIGS. 6B-6I, linear stretch zones may be configured as lines or strands of elastomer generally having widths less than about 2 mm and typically less than about 1 mm. Linear stretch zones 618 may also be configured as bands of elastomer generally having widths between about 2 mm and about 40 mm and aspect ratios ranging from about 2:1 to about 100:1. Linear stretch zones 618 may also be disposed at an angle with respect to the lateral centerline 651 (as shown in FIG. 6A). In certain embodiments, angles may be in the range 0±70°. Stretch zones having a predominately lateral orientation are generally wider and have a higher modulus than those having a generally longitudinal orientation. Curved stretch zones 620 may be either concave or convex with respect to the longitudinal or lateral centerlines 650, 651, or both and may have radii of curvature greater than about 1 mm, preferably greater than about 10 mm, more preferably greater than about 50 mm. The curvature may optionally be variable over the length or "path" of the stretch zone 620. In suitable embodiment, the thickness of the elastomer within the stretch zones 618 and/or 620 may be in the range of about 0.02 mm to about 5 mm; however, stretch zones with thicknesses outside of this range are feasible.

Figure 6B:
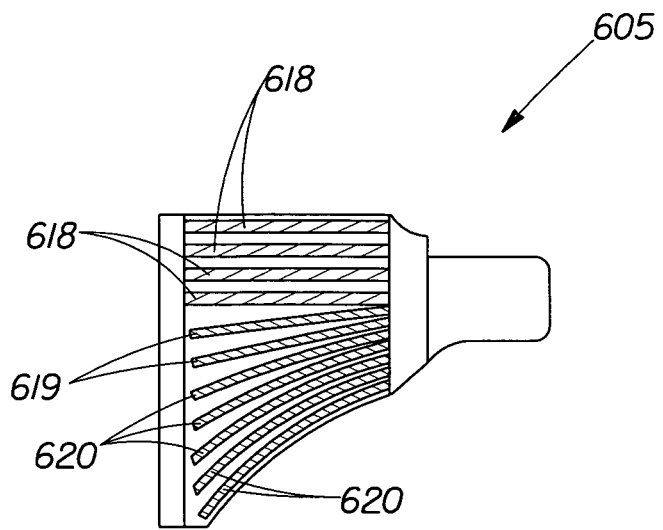
Figure 6C:
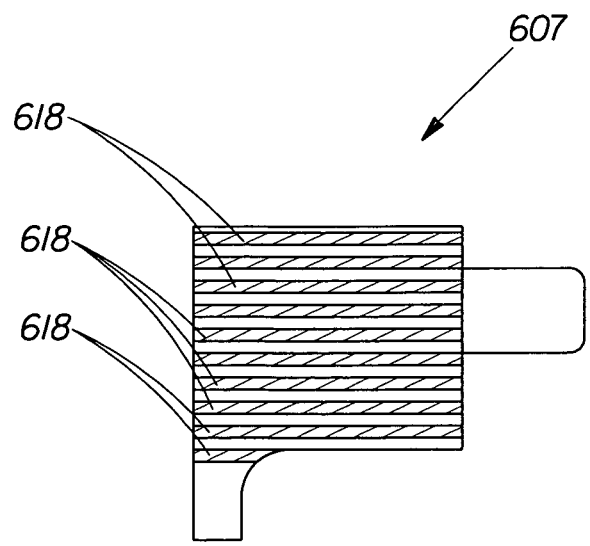
Figure 6D:
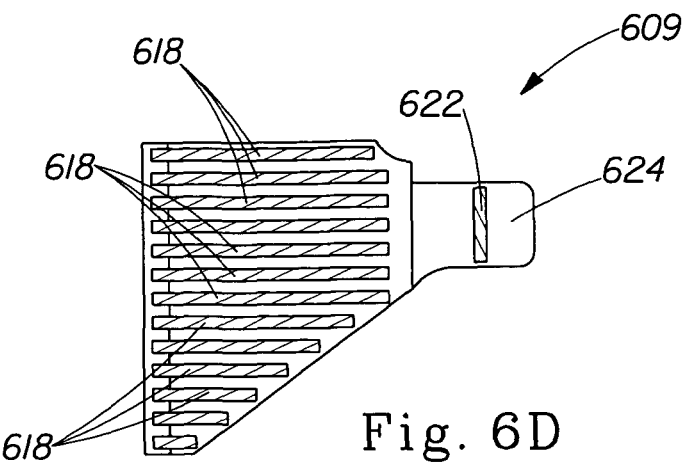
Figure 6E:
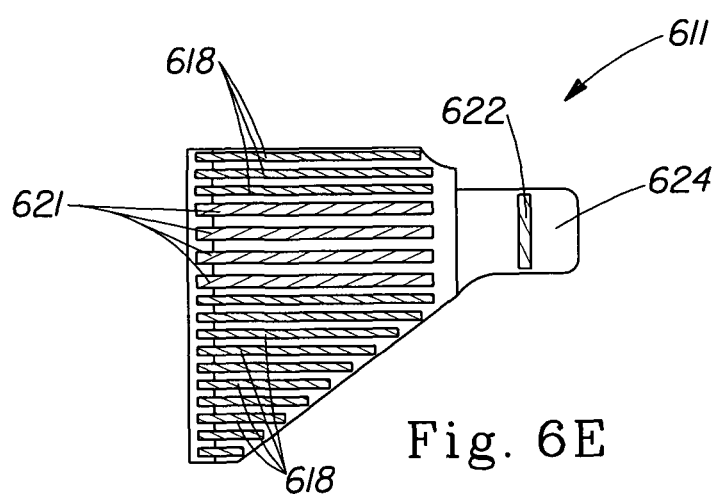
Figure 6F:
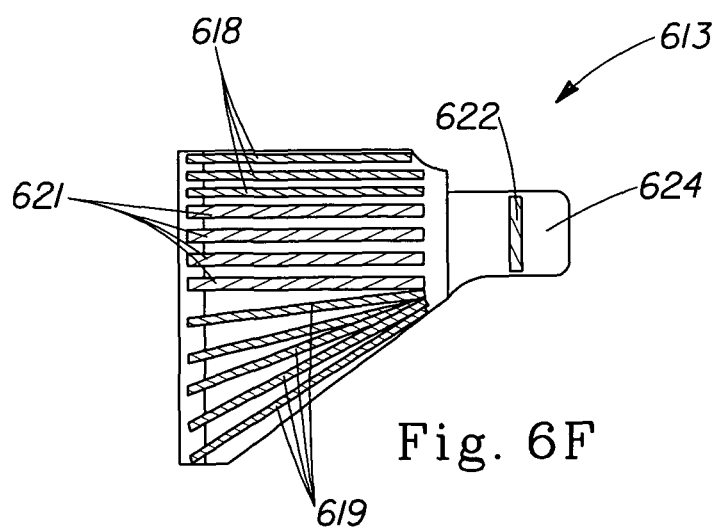
Figure 6G:
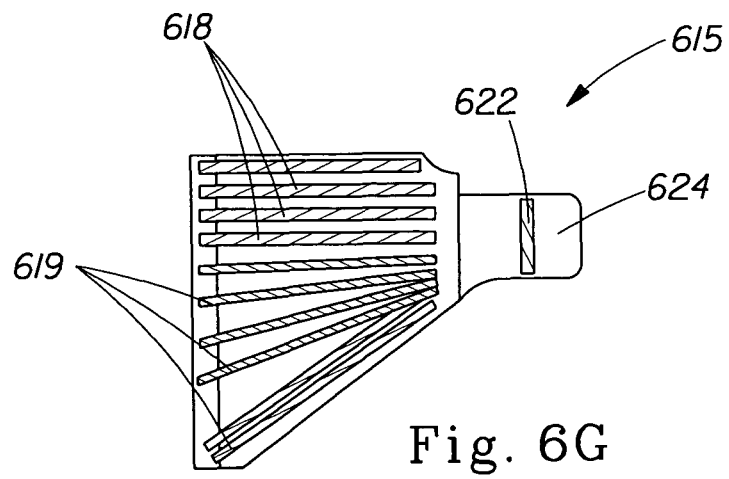
Figure 6H:
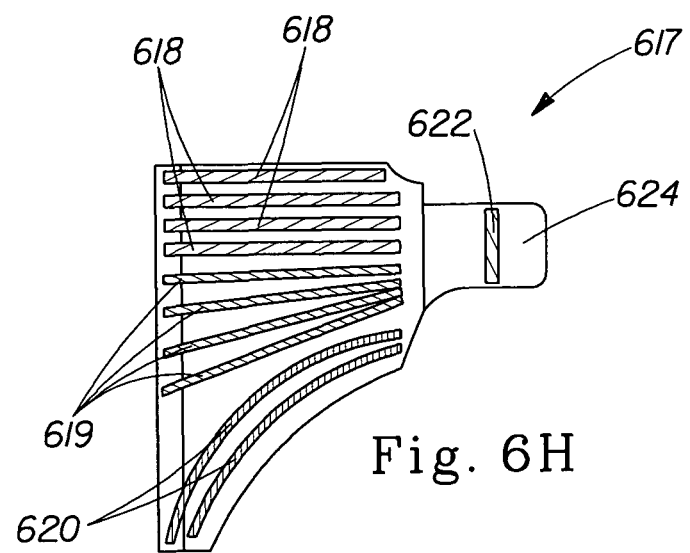
Figure 6I:
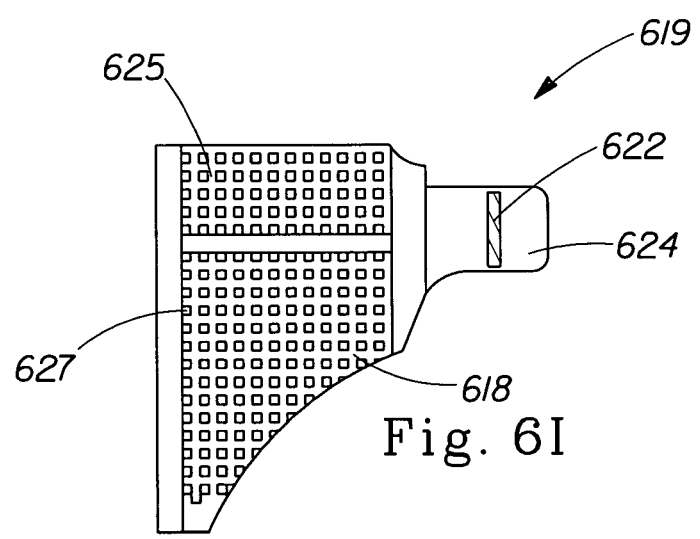

Exemplary embodiments of the invention are shown in FIG. 6B with side panel 605, FIG. 6C with side panel 607, FIG. 6D with side panel 609, FIG. 6E with side panel 611, FIG. 6F with side panel 613, FIG. 6G with side panel 615, FIG. 6H with side panel 617, and FIG. 6I with side panel 629. The side panels 605, 607, 609, 611, 613, 615, 617, and 629 may be integral with or separately attached to the diaper chassis of the diaper 10 or 250 or pant 370 described previously. At least one of the stretch zones 618, 619, 620, 621 comprises the slow recovery elastomeric composition as described herein. FIGS. 6B and 6H show side panel 605 and 617, respectively, having linear stretch zones 618, linear stretch zones 619 disposed at an angle from the lateral center line 651 (as shown in FIG. 6A), and curvilinear stretch zones 620. FIGS. 6C-D show side panel 607, 609 having linear stretch zones 618. FIGS. 6E-F show side panels 611, 613 having linear stretch zones 618, 621. Stretch zones 618 and 621 may differ in physical property, composition, geometry, relative orientation, spacing, or elasticity or extensibility. For example, stretch zone 621 may differ from stretch zone 618 with respect to area. FIG. 6F shows side panel 613 further having linear stretch zones 619 disposed at an angle to the lateral centerline 651 (as shown in FIG. 6A). FIG. 6G shows side panel 615 having linear stretch zones 618 and linear stretch zones 619 disposed at various angles from the lateral center line 651 (as shown in FIG. 6A)

FIG. 6I shows side panel 629 comprises a pair of cross hatch arrays 625, 627. As shown therein, both of arrays 625, 627 comprise a plurality of linear stretch zones 618 in an overlapping, cross hatch pattern where the individual stretch zones 618 have either a predominately lateral orientation or a predominately longitudinal orientation. As will be recognized and described herein, the stretch zones 618 can also be at an angle other than 0° or 90° with respect to the centerlines.

In one embodiment of side panel 629 shown in FIG. 6I, array 625 may have different mechanical properties than array 627. In particular, first array 625 may comprise a slow recovery elastomer whereas the second array 627 may comprise a "traditional" elastomer. Alternatively, first array 625 may have a first thickness of slow recovery elastomer, while second array 627 may have a second thickness of slow recovery elastomer different than the first thickness.

Furthermore, FIGS. 6D-I show additional stretch zone 622 applied to or formed as part of the fastener element 624 to impart other desired elastic properties of the present invention. Additional stretch zone 622 may also comprise the slow recovery elastomeric composition as described herein.

Alternatively, one or more of stretch zones 618, 619, 620, 621 may comprise an elastomeric composition that differs from the composition used to form any other stretch zones 618, 619, 620, 621. A subset of stretch zones 618, 619, 620, 621 may be taken as an array. For example, referring to FIG. 6B, certain stretch zones 618 that lie longitudinally outboard (i.e., closer to rear waist end 635 as shown in FIG. 6A) of the remainder of stretch zones 619, 620 may comprise a slow recovery elastomer so as to provide a slow recovery characteristic, while other stretch zones 619 and/or 620 may comprise a traditional elastomer or an elastomer exhibiting a different recovery (i.e., having differing post elongation strain for some unit time as measured by the Post Elongation Recovery Test) than that of the elastomeric composition of stretch zones 618.

Alternatively, an array of linear stretch zones 618, 619, 621; curved stretch zones 620; or both may comprise a spiral or an overlapping or entangled configuration, for example a cross hatch array. Suitable stretch zone and/or array shapes include rectangles, circles, ellipses, diamonds, triangles, parallelograms, trapezoids, wedges or other sections of circles or ellipses, other polygons, or other irregular enclosed shapes.

Figure 7A:
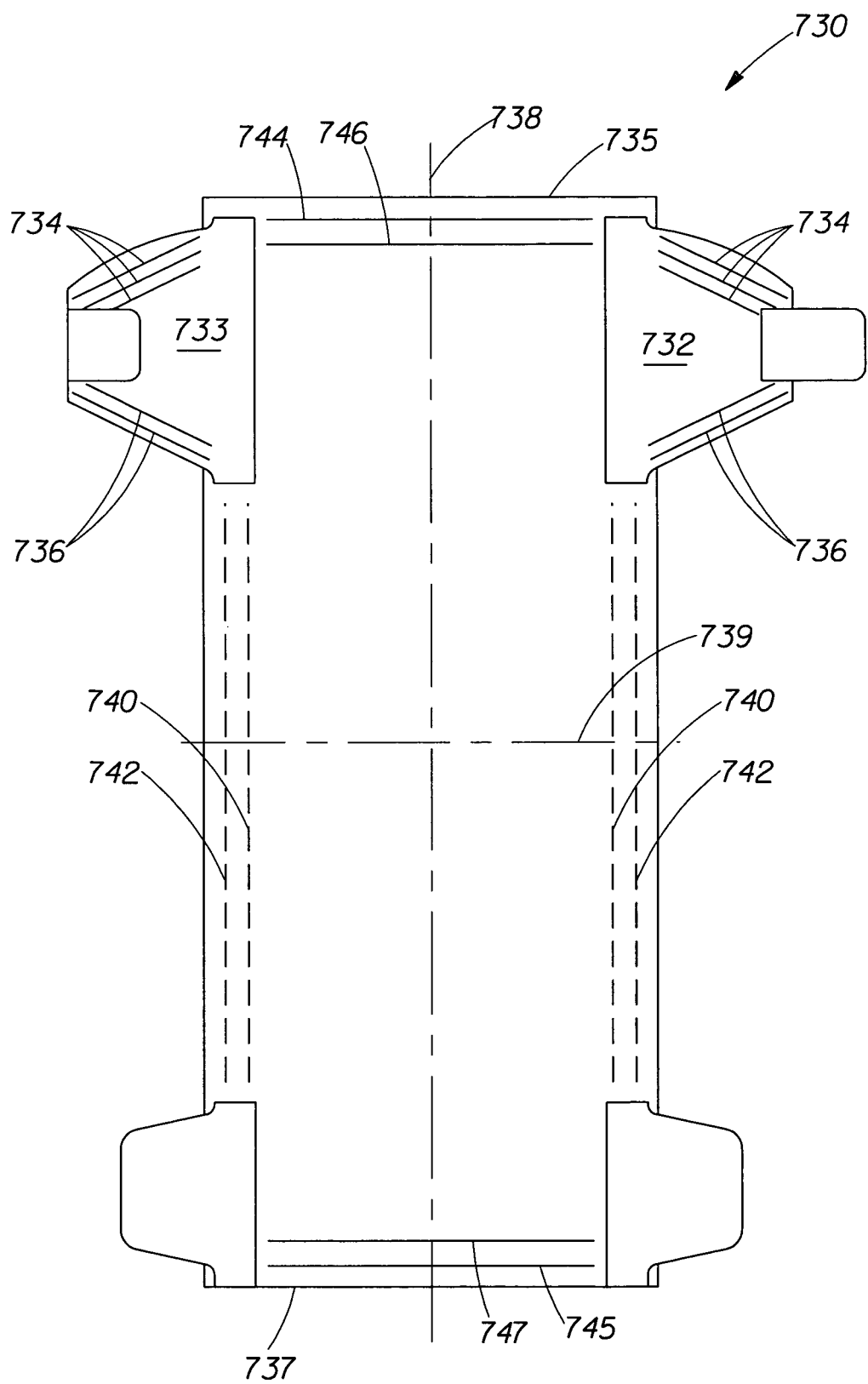
FIGS. 7A and 7B show yet another embodiment of a diaper in accordance with invention wherein stretch zones are provided to the ears and along the absorbent assembly for imparting the desired elastic properties to the diaper.
Figure 7B:
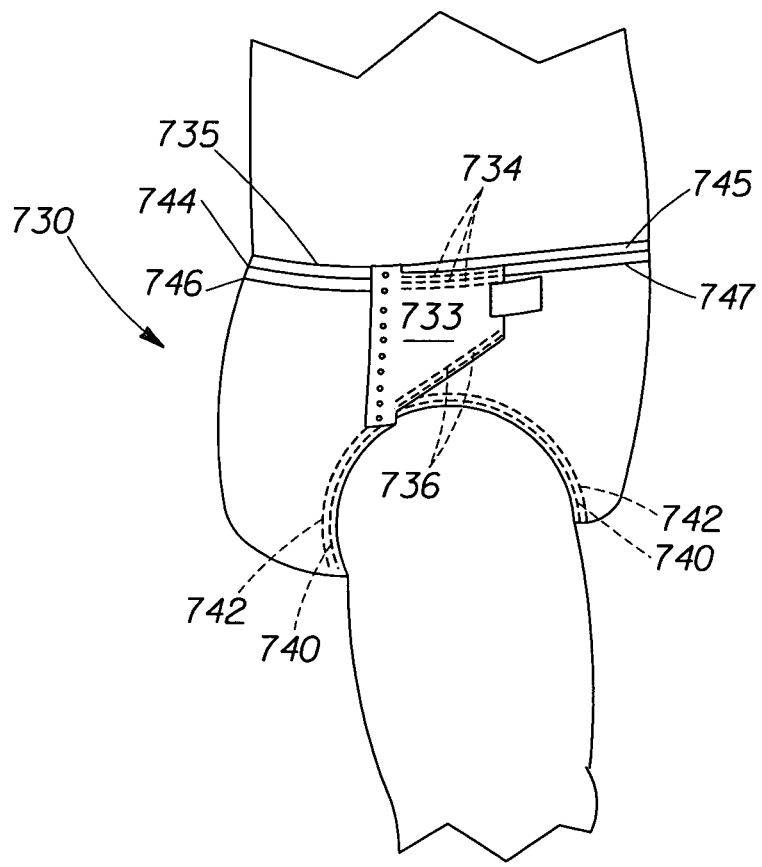

Referring to FIGS. 7A and 7B, a diaper 730, similar to diaper 10 and having a longitudinal centerline 738, a lateral centerline 739, a rear waist end 735 and a front waist end 737, is depicted in which the waist and thigh portions of the side panel 732, 733 preferably comprise different stretch zones 734 and 736, varying in tension, elastomeric composition, and/or angle as shown. In certain embodiments, the side panel stretch zone 734 nearer the rear waist end 735 of diaper 730 may be oriented at an angle of about 0 to about minus 50 degrees from the lateral centerline 739, more preferably between about −5 degrees and about −40 degrees from the lateral centerline 739. In suitable embodiments, the stretch zone 736 may be oriented at an angle of about 0 to about plus 70 degrees from the lateral centerline 739, more preferably between about +20 degrees and about +60 degrees from the lateral centerline 739. In one exemplary embodiment, side panel 732 stretch zone embodiment includes a stretch zone 734 oriented at about −10 to −20° from the lateral centerline 739 and a stretch zone 736 oriented at about +20° to +50° from the lateral centerline 739.

In certain embodiments, at least one of the stretch zones 736 may be aligned with the end of the outer leg cuff elastics 740, 742 in order to provide an effective extension of the leg cuff elastic, thereby encircling a wearer's leg with a combination of stretch zone 736 and 740, 742 shown in FIG. 7B. That is, the outer leg cuff elastics 740, 742 and the side panel stretch zones cooperate to provide a substantially continuous line of force to encircle a wearer's legs.

In other embodiments, at least one of the waist regions adjacent rear waist end 735 or front waist end 737 is also provided with one or more waist stretch zones 744, 745, 746, 747. In such embodiments the waist stretch zones 744, 745, 746, 747 may be aligned with stretch zones 734 that are disposed so as to provide a substantially continuous line of force encircling a wearer's waist as can be more clearly seen in FIG. 7B. Depending on the design of diaper 730, such a line of force may follow the low motion zone of a wearer (see below) or be juxtaposed with another portion of a wearer's anatomy while encircling the waist.

Regardless of the specific construction, composition, or geometry, or stretch properties of the side panel 732, the stretch zones 734 and 736 in the waist and thigh portions are preferably capable of substantially independent action with respect to one another. Certain embodiments may include an additional side panel stretch zone (not shown) functioning as a transition between the leg and thigh portions, i.e., a "transition zone". The transition zone may have distinctly different stretch properties (or even not be elastic at all) than either the leg or waist zones and functions to decouple or separate the deformations caused by the leg and waist panels, allowing them to act independently without interaction with each other. In embodiments comprising a side panel transition zone, the transition zone may be substantially extensible to further promote independent action between the waist and thigh zones of the side panel, while still providing sufficient stretch to accommodate the relative movements of the waist and thigh zones while being worn by a wearer, helping to control buckling and/or folding of the transition region.

Any of the stretch zones 734, 736, 744, 745, 746, 747 and/or transition zones may comprise the slow recovery elastomer as disclosed herein.

Figure 8A:
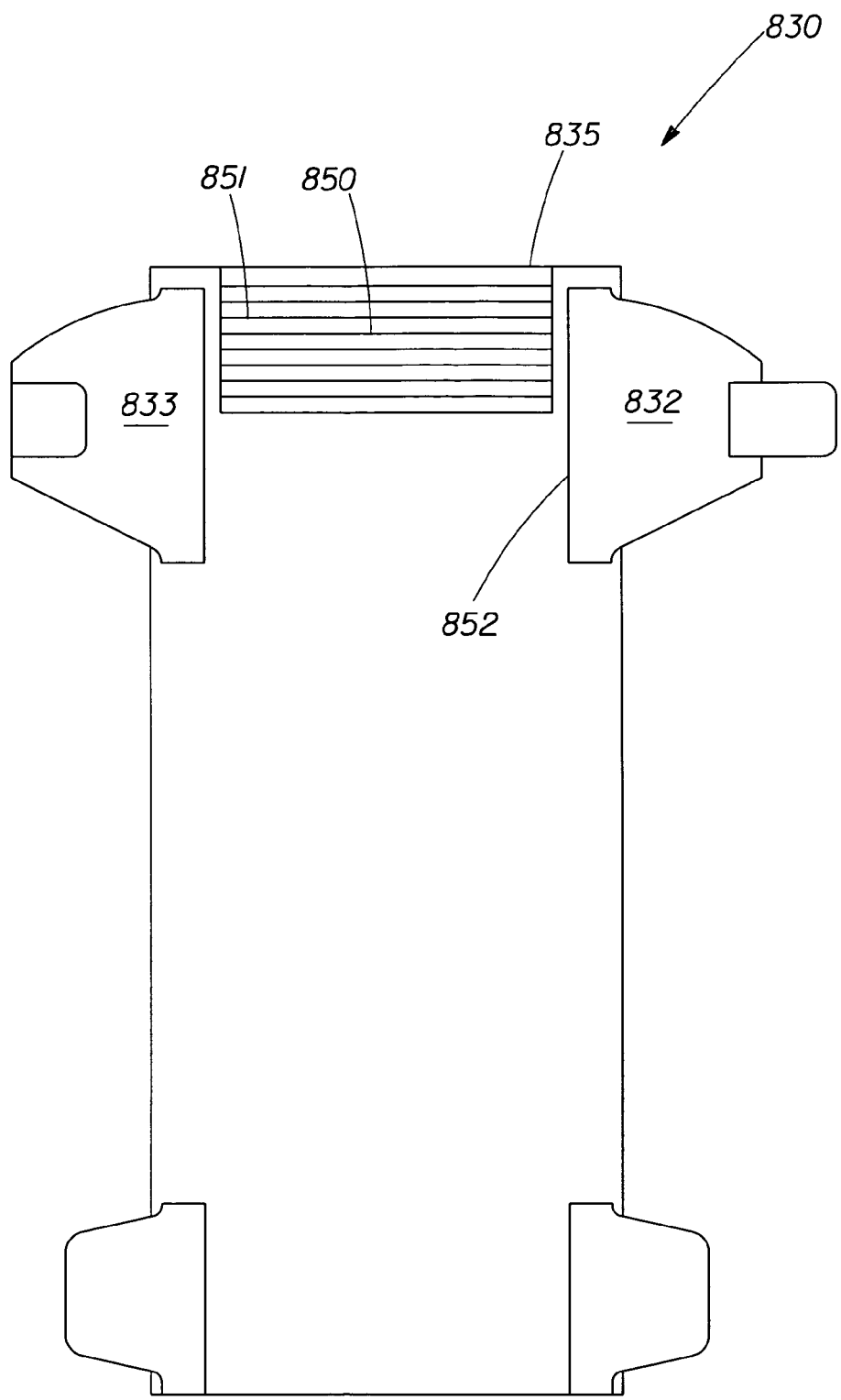
FIGS. 8A-D illustrates diapers in which stretch zones are disposed in a variety of locations to provide several alternative designs for improved wearer comfort and fit.
Figure 8B:
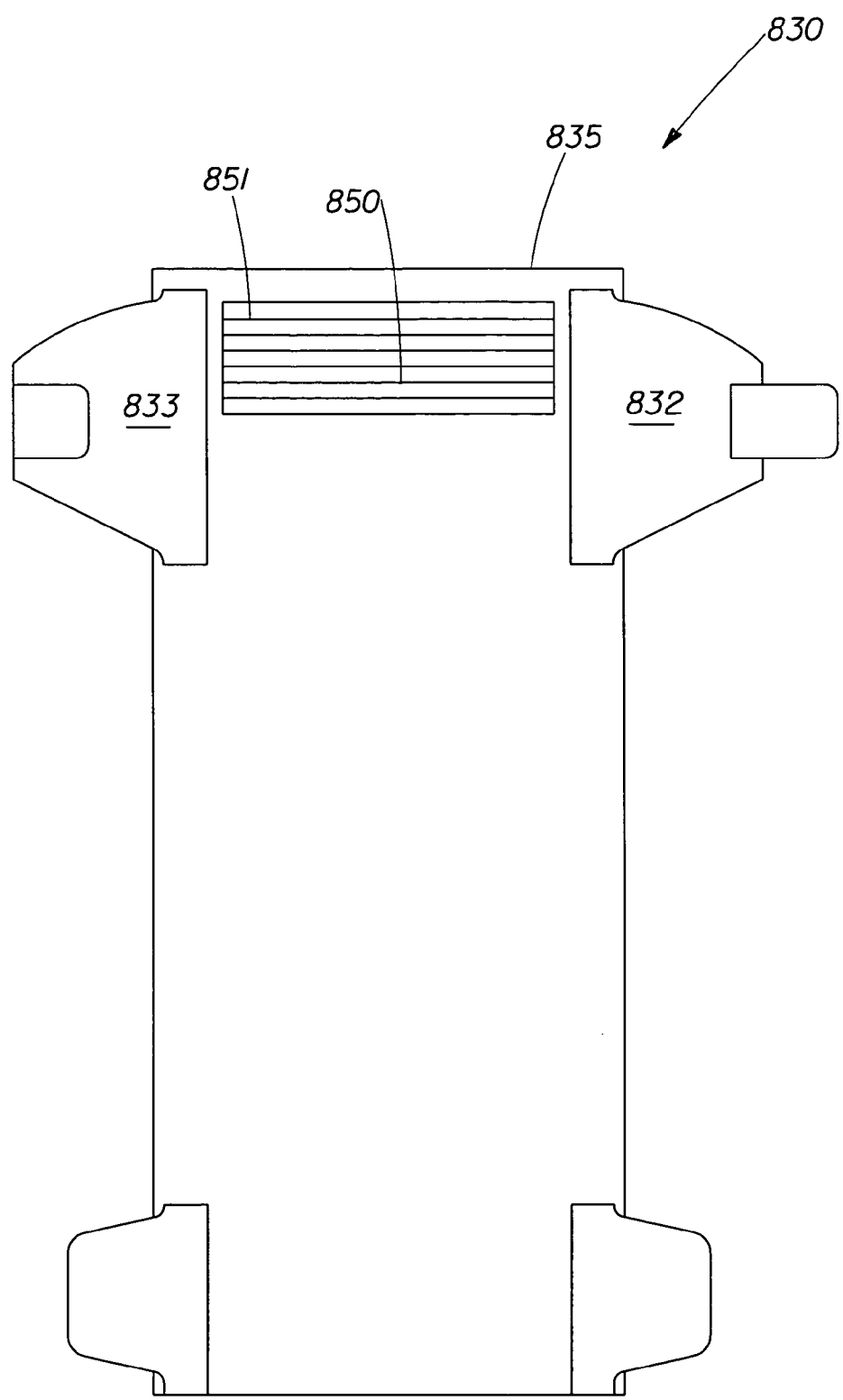

Referring to FIGS. 8A-D, at least one array 850 of stretch zones 851 may be included in the waist region of the diaper 830. The array 850 of stretch zones 851 may have similar or varying degrees of elasticity or extensibility and may assume any geometry or orientation. For example, array 850 may comprise stretch zones 851 where two stretch zones have differing elastomeric compositions. Generally, at least one stretch zone 851 will comprise the slow recovery elastomer as disclosed herein. The array 850 of stretch zones 851 may comprise the slow recovery elastomer as disclosed herein. For example, in FIG. 8A the array 850 of stretch zones 851 is located at the waist end 835 of diaper 830, whereas FIG. 8B shows another embodiment in which the array 850 is offset from waist end 835. It may be preferable to have array 850 located generally in the lower back waist area as shown on a partial side view of wearer 852 in FIG. 8C. In this way, the maximum fit and comfort will be experienced by the wearer 852 as the tension is applied by the article to the wearer's body at or immediately above the convexity of the buttocks (i.e., the "buttocks shelf"), contributing to the overall anchoring capability of the article (i.e., its ability to resist sagging). Said another way, the array 850 and stretch zones 862, 864, 866, 868 and 870 (shown in FIG. 8D) co-operate to maintain diaper 830 in an optimal fit configuration with respect to the low motion zone 853 (i.e., the line or zone connecting the lumbar curve of the back over the hips to under the abdominal crease of a wearer's body 852) so as to maximize the performance thereof. For a more detailed discussion of low motion zones see U.S. Pat. No. 5,358,500.

Figure 8C:
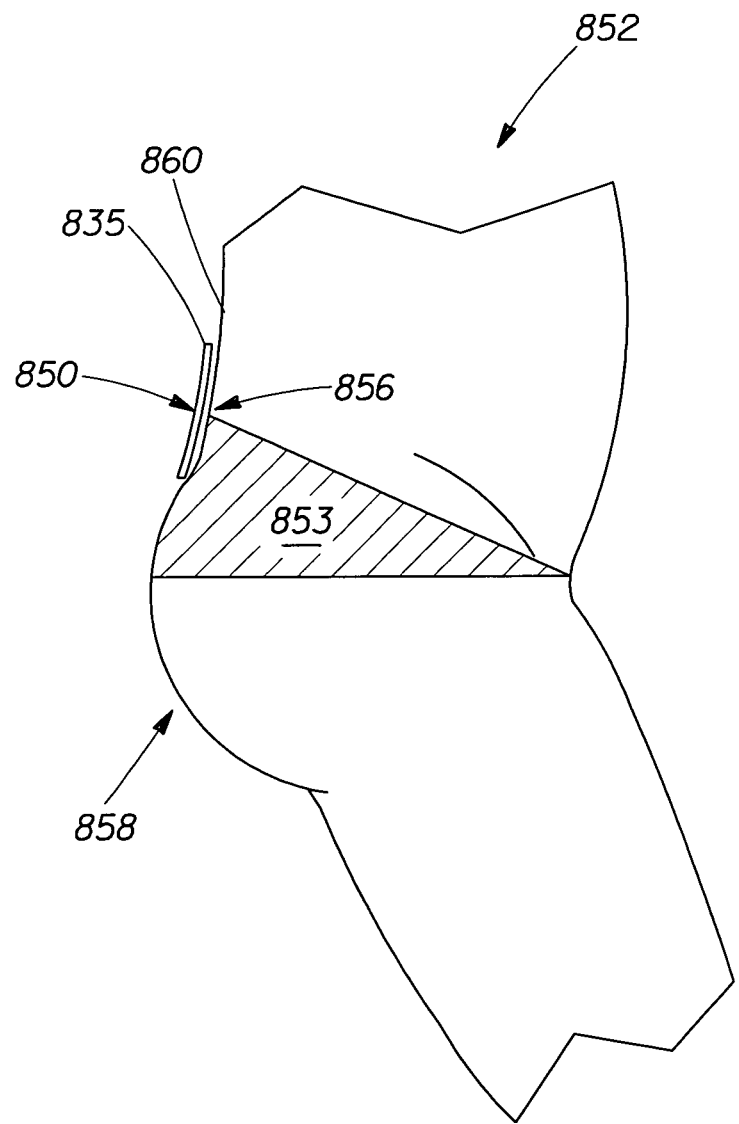
Figure 8D:
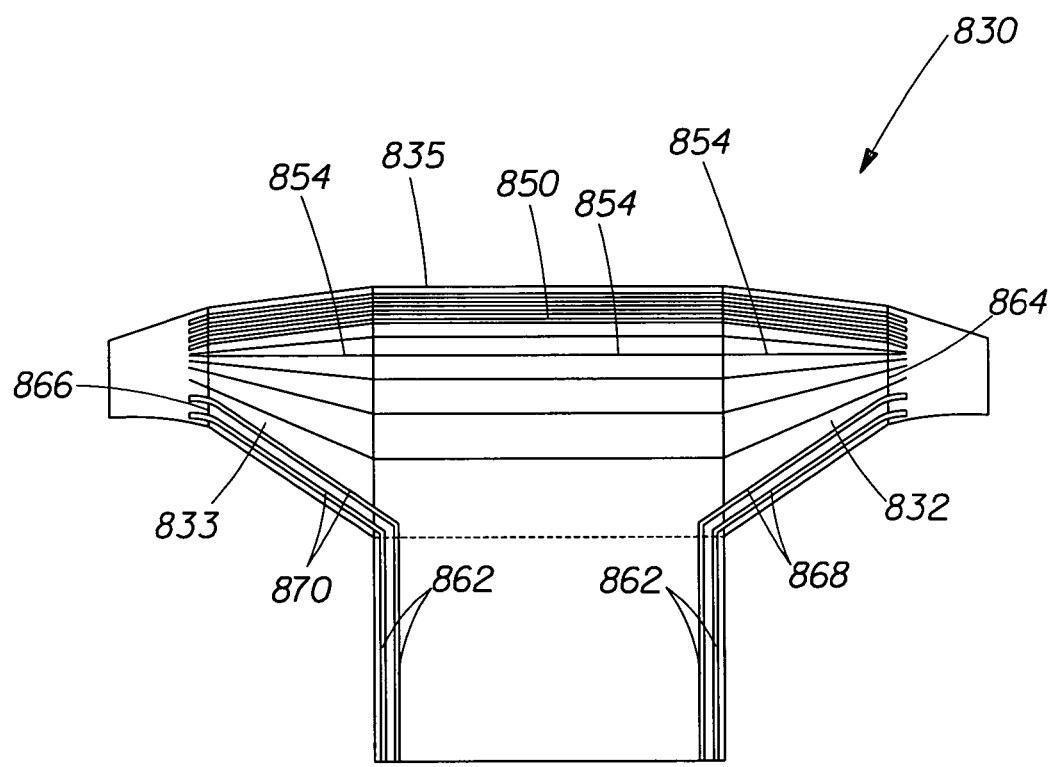

In certain embodiments as exemplified in the partial plan view of diaper 830 in FIG. 8D, array 850 may comprise one or more stretch zones 854 having higher localized elastic resistances (i.e., a "high tension" stretch zone 854) aligned with the waist end 835. The high-tension stretch zones 854 may be adjacent the waist end 835 or may be disposed inboard thereof. The high-tension stretch zones 854 may be disposed between about zero and 30 mm from the waist end 835 of the diaper 830. In other embodiments, the high-tension stretch zones 854 are disposed less than about 20 mm from the waist end 835. An array 850 of the high-tension stretch zones 854 may correspond to an area 856 on the wearer 852 body, as shown in FIG. 8C, immediately above or at the upper curvature of the buttocks 858 where the high-tension stretch zone 854 functions to provide additional anchoring capability for the diaper 830 by applying a normal force to the geometric "shelf" created by the buttocks 858. The high tension stretch zones 854 additionally hold the waist end 835 of the diaper 830 against the wearer's back 860 preventing back waist gapping.

In embodiments comprising an array 850 of stretch zones 854 at or near the waist end 835 of diaper 830 and extending through multiple regions of the back waist and crotch of the article, the remaining area of the waist end 835 may have either a lower elastic resistance, may be primarily extensible, or may comprise areas with either property. In any case, this waist end 835 area (i.e., the area not including the stretch zones 850 or 854) may be a low-tension zone.

Figure 9:
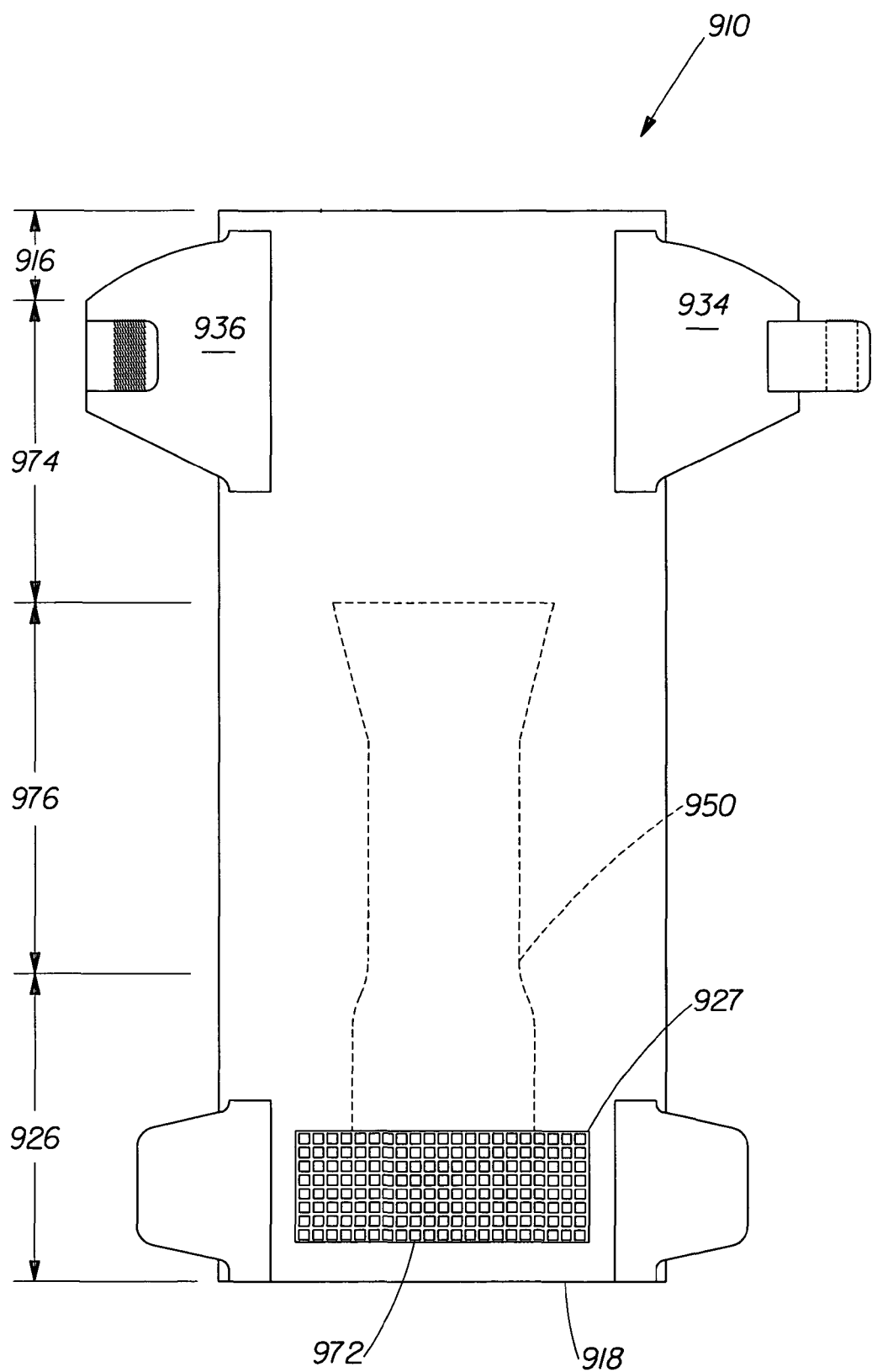
FIG. 9 is a plan view of a diaper in accordance with the invention in which stretch zones are provided in the diaper ears and a waist portion.

Referring again to FIG. 8D, stretch zones 862 may be substantially parallel to the proximal edges 864 and 866 of side panels 832 and 833, respectively. Optionally, transition stretch zones 868 and 870 may be disposed intermediate stretch zones 854 and 868, 870. The stretch zone 854 may provide a primary anchoring function and stretch zones 862, 868 and 870 may provide a dynamic leg motion accommodation function. While stretch zones 854, 862, 868 and 870 all provide an elastic resistance, the present invention allows tailoring such forces in both to degree and direction to meet the different needs of the anchoring and motion accommodation functions. Referring to FIG. 9, diaper 910 is depicted with a front waist region 926 that may comprise at least one stretch zone 972. The function of stretch zone 972 is to dynamically accommodate the contraction and expansion cycles of the wearer's abdomen as the wearer moves and/or changes position, preventing front waist sagging. Stretch zone 972 may be substantially aligned with the front waist end 918 of the diaper 910. In certain embodiments, diaper 910 may include a fastening landing zone 927 disposed in or near the front waist end 918. In these embodiments, stretch zone 972 may at extend into, overlap, comprise a portion of, or be bounded by the landing zone 927, as shown in FIG. 9.

While a buttocks region 974 located in proximity to a crotch region 976 as shown on diaper 910 may comprise elastic portions, extensible portions, or a combination thereof; the buttocks region 974 may be provided with a pattern of elastomer so as to provide a low level of elastic resistance to a stretch zone therein causing the buttocks region 974 to better conform to a wearer's anatomy so as to accommodate the largest wearer circumference (i.e., the buttocks any may include the volume of the absorbent core 950) and allowing the buttocks region 974 to have a lower on-wearer tension than the rear waist end 916 region. The buttocks region 974 may have stretch zones with extensibility that allows for a smoother geometric transition from the constricted crotch region 976 between the wearer's legs to the side panels 934 and 936 which may have stretch zones similar to those described in FIG. 8D for anchoring. The buttocks region 974 preferably may elongate further than the waist end 916 region to accommodate the wearer's anatomic shape.

Figure 10:
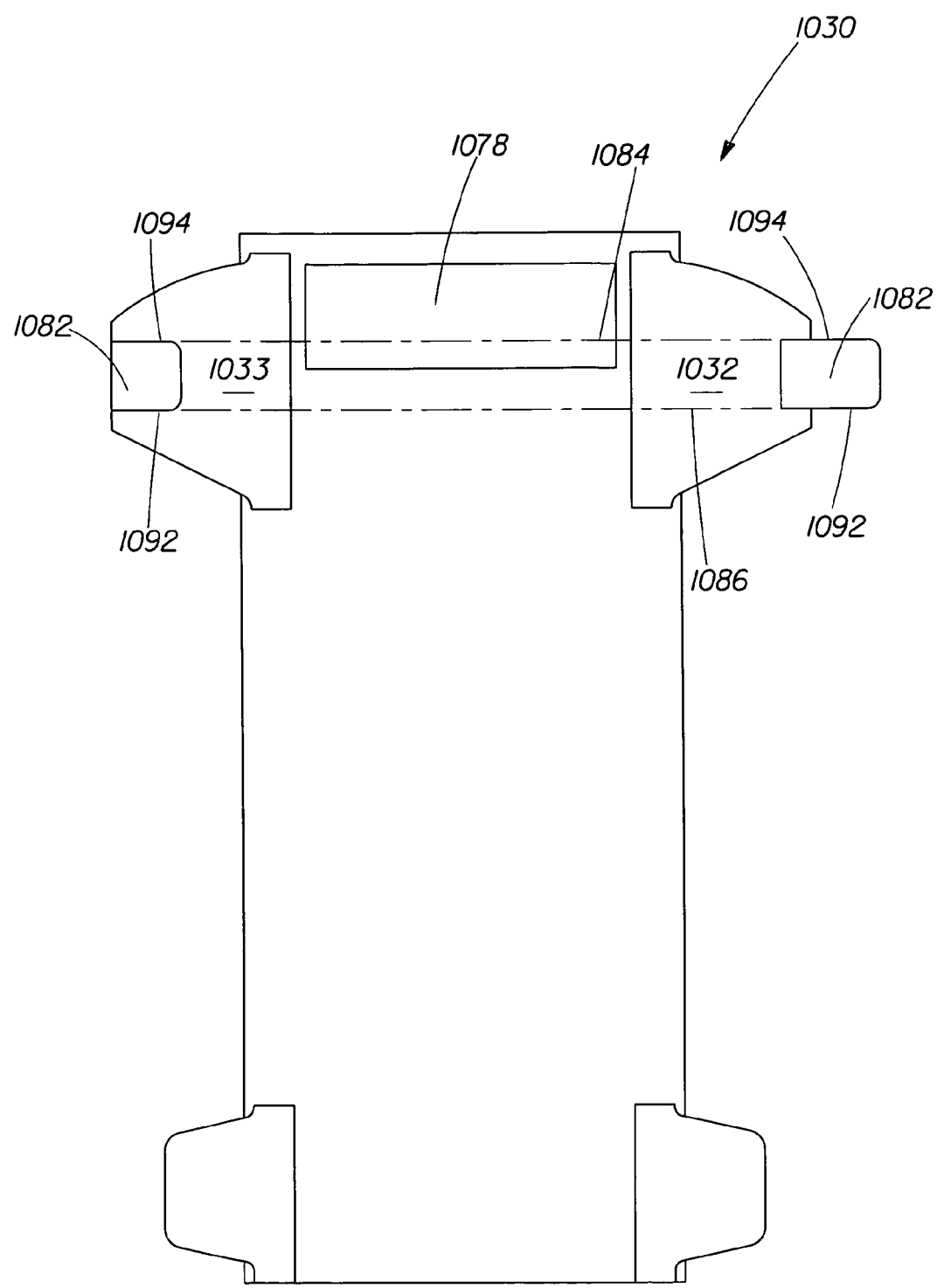
FIG. 10 is a plan view of a diaper in accordance with the invention in which the stretch zones are provided in the rear waist portion such that there is at least partial longitudinal alignment with the diaper ears.

Referring to FIG. 10, another embodiment of diaper 1030 is shown in which array 1078 in the waist region may be preferably aligned with side panels 1032 and 1033 and/or the fasteners 1082 disposed on side panels 1032 and 1033 in order to create a substantially continuous line of tension around the waist to promote conforming sustained fit. The array 1078 may at least partially overlap one of the two imaginary lines 1084 and 1086 that connect the longitudinally outboard edges 1092, 1094 of fasteners 1082.

Figure 11:
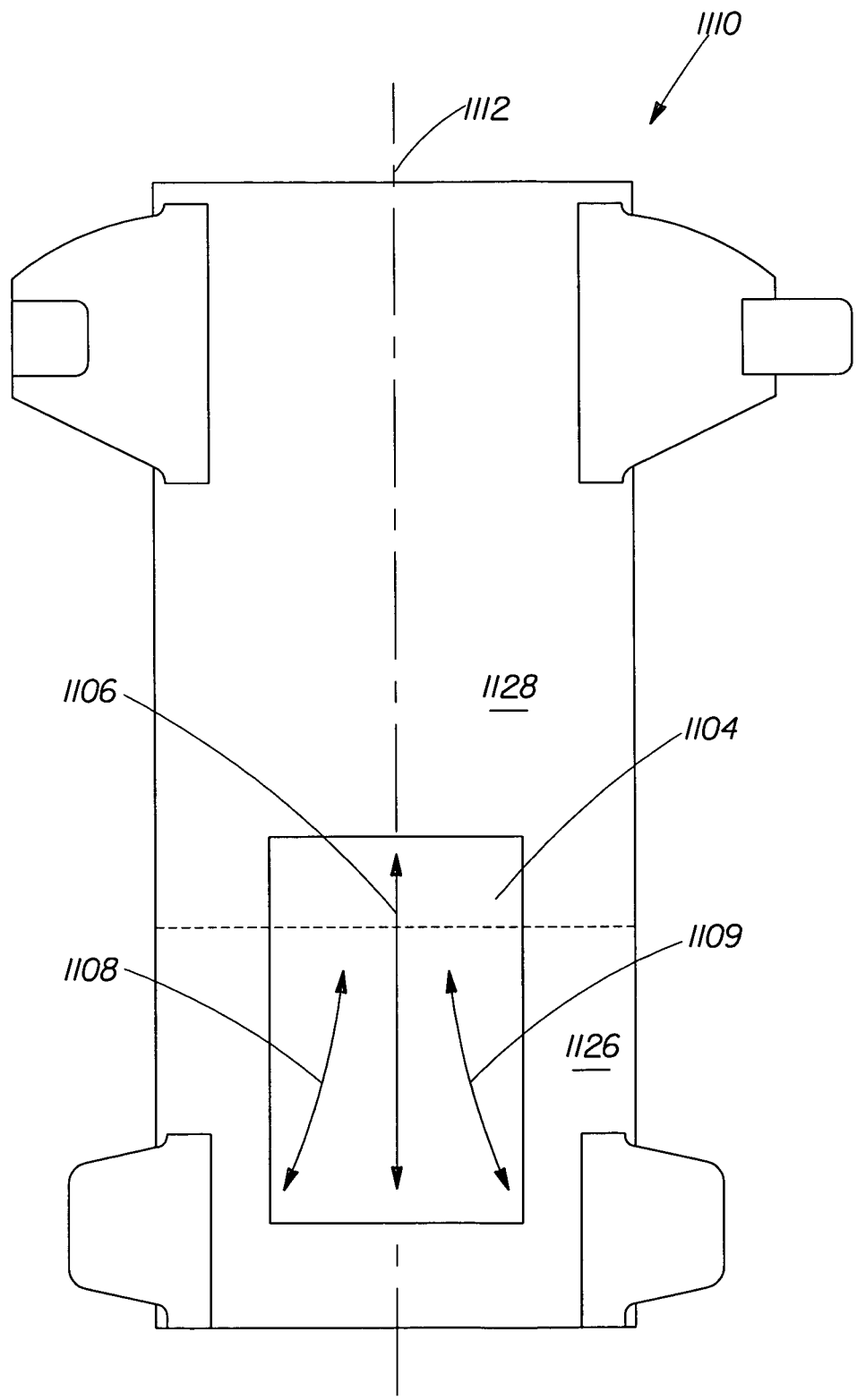
FIG. 11 is a plan view of a diaper having stretch zones in the front crotch portion in accordance with the invention.

Referring to FIG. 11, an array 1104 is shown on diaper 1110 in a crotch region 1128 spanning into a front waist region 1126. The stretch zones comprising array 1104 may be primarily parallel to longitudinal centerline 1112 of the diaper 1110 allowing better fit in the front crotch region 1128 by providing an elastic resistance along the centerline 1112 as depicted by arrow 1106. Array 1104 ideally will have a low elastic resistance so as not to pull the front of diaper 1110 down, resulting in sagging. Array 1104 may also comprise stretch zones laterally outboard of and at an angle to the longitudinal centerline 1112 and diverging toward the front corners of diaper 1110 as shown by arrows 1108 and 1109.

Figure 12:
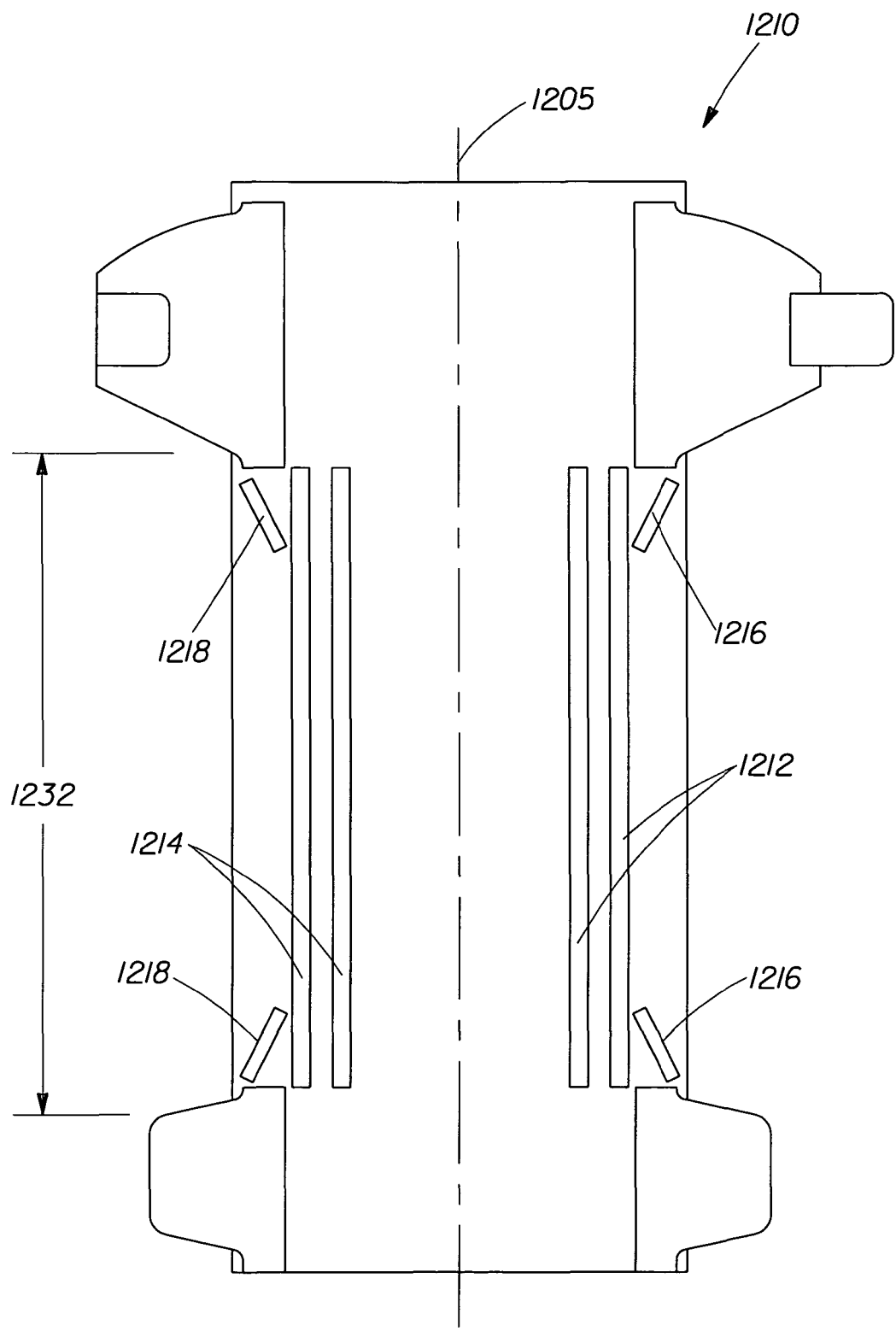
FIG. 12 is another plan view of a diaper in which stretch zones are disposed along the lateral portions of the diaper in order to provide the desired elastic properties in the leg openings.

Referring to FIG. 12, another embodiment, diaper 1210 is shown in which leg regions 1232 may comprise stretch zones 1212 and 1214. The stretch zones 1212 and 1214 may be substantially parallel to longitudinal centerline 1205. Alternatively, stretch zones 1212 and 1214 may also be curvilinear or at an angle to the longitudinal centerline 1205. Portions of the leg regions 1232 may comprise one or more additional extensible stretch zones 1216 and 1218 that are oriented at an angle to the longitudinal centerline 1205 of diaper 1210. In suitable embodiments, stretch zones 1216 and 1218 may be at an angle of about 45 degrees to about 90 degrees from the longitudinal centerline 1205. The stretch zones 1216 and 1218 may be at an angle of 45 to 60 degrees from the longitudinal centerline 1205.

The embodiments in FIGS. 1-12 have diaper components which may take any one or more of the materials, designs, and methods of assembly described hereinafter without departing from the scope of the present invention. While any of the article components may be assembled in a variety of well known configurations, exemplary diaper configurations are described generally in U.S. Pat. No. 3,860,003; U.S. Pat. No. 5,151,092; and U.S. Pat. No. 5,221,274; and U.S. Pat. No. 5,554,145; U.S. Pat. No. 5,569,234; U.S. Pat. No. 5,580,411; and U.S. Pat. No. 6,004,306.

Exemplary breathable materials may include materials such as woven webs, nonwoven webs, composite materials such as film-coated nonwoven webs, microporous films such as manufactured by Mitsui Toatsu Co., of Japan under the designation ESPOIR NO and by Exxon Chemical Co., of Bay City, Tex., under the designation EXXAIRE, and monolithic films such as manufactured by Clopay Corporation, Cincinnati, Ohio under the name HYTREL blend P18-3097 Some breathable composite materials are described in greater detail in U.S. Pat. No. 6,187,696; U.S. Pat. No. 5,938,648; U.S. Pat. No. 5,865,823; and U.S. Pat. No. 5,571,096.

The article may include a structural elastic-like film web that is an extensible material that exhibits an elastic-like behavior in the direction of elongation without the use of added elastic materials and is described in more detail in U.S. Pat. No. 5,518,801. In alternate embodiments, the backsheets may comprise elastomeric films, foams, strands, or combinations of these or other suitable materials with nonwovens or synthetic films.

Exemplary absorbent structures for use as the absorbent core are described in U.S. Pat. No. 4,610,678; U.S. Pat. No. 4,673,402; U.S. Pat. No. 4,834,735; U.S. Pat. No. 4,888,231; U.S. Pat. No. 5,137,537; U.S. Pat. No. 5,147,345; U.S. Pat. No. 5,342,338; U.S. Pat. No. 5,260,345; U.S. Pat. No. 5,387,207; and U.S. Pat. No. 5,625,222.

Suitable absorbent and nonabsorbent sublayers are described in European Patent Application No. EP 0 847 738 A1 and U.S. Pat. No. 5,941,864. Further, the sublayer, or any portion thereof, may include or be coated with a lotion or other known substances to add, enhance or change the performance or other characteristics of the element.

Some exemplary surface fastening systems are disclosed in U.S. Pat. No. 3,848,594; U.S. Pat. No. 4,662,875; U.S. Pat. No. 4,846,815; U.S. Pat. No. 4,894,060; U.S. Pat. No. 4,946,527; the herein before referenced U.S. Pat. No. 5,151,092; and U.S. Pat. No. 5,221,274. An exemplary interlocking fastening system is disclosed in U.S. Pat. No. 6,432,098. The fastening system may also provide a means for holding the article in a disposal configuration as disclosed in U.S. Pat. No. 4,963,140; include primary and secondary fastening systems, as disclosed in U.S. Pat. No. 4,699,622; provide a means to reduce shifting of overlapped portions or to improve fit as disclosed in U.S. Pat. No. 5,242,436; or provide a means to resist gapping at a wearer's belly as disclosed in U.S. Pat. Nos. 5,499,978, 5,507,736, and 5,591,152.

Suitable absorbent articles having an elastic waist feature may be constructed in a number of different configurations including those described in U.S. Pat. Nos. 4,515,595; 4,710,189; 5,151,092; and 5,221,274.

Suitable training pants and pull-on diapers are disclosed in U.S. Pat. No. 5,246,433; U.S. Pat. No. 5,569,234; U.S. Pat. No. 6,120,487; U.S. Pat. No. 6,120,489; U.S. Pat. No. 4,940,464; and U.S. Pat. No. 5,092,861.

Examples of diapers with elasticized side panels are disclosed in U.S. Pat. No. 4,857,067; U.S. Pat. No. 4,381,781; U.S. Pat. No. 4,938,753; the herein before referenced U.S. Pat. No. 5,151,092; U.S. Pat. No. 5,221,274; U.S. Pat. No. 5,669,897; U.S. Pat. No. 6,004,306, and the aforementioned U.S. Pat. No. 6,300,208.

U.S. Pat. No. 3,860,003 describes a disposable diaper which provides a contractible leg opening having a side flap and one or more elastic members to provide an elasticized leg cuff (a gasketting cuff). U.S. Pat. Nos. 4,808,178 and 4,909,803 describe disposable diapers having "stand-up" elasticized flaps (barrier cuffs) which improve the containment of the leg regions. U.S. Pat. Nos. 4,695,278 and 4,795,454 describe disposable diapers having dual cuffs, including gasketting cuffs and barrier cuffs.

Embodiments of the present invention may also include pockets for receiving and containing waste, spacers which provide voids for waste, barriers for limiting the movement of waste in the article, compartments or voids which accept and contain waste materials or any combinations thereof. Examples of pockets and spacers for use in absorbent products are described in U.S. Pat. No. 5,514,121; U.S. Pat. No. 5,171,236; U.S. Pat. No. 5,397,318; U.S. Pat. No. 5,540,671; U.S. Pat. No. 6,168,584; U.S. Pat. No. 5,306,266; and U.S. Pat. No. 5,997,520. Examples of compartments or voids are disclosed in U.S. Pat. No. 4,968,312; U.S. Pat. No. 4,990,147; U.S. Pat. No. 5,062,840; and U.S. Pat. No. 5,269,755. Examples of suitable transverse barriers are described in U.S. Pat. No. 5,554,142; U.S. Pat. No. 6,010,490; and U.S. Pat. No. 5,653,703. Examples of other structures especially suitable for management of low viscosity feces are disclosed in U.S. Pat. Nos. 5,941,864; 5,977,430; and 6,013,063.

The diaper 10 of FIG. 1 is preferably applied to a wearer by positioning one of the waist regions under the wearer's back and drawing the remainder of the diaper between the wearer's legs so that the other waist region is positioned across the front of the wearer. The fastener elements may then be used by the caregiver to join the front and rear waist regions so as to encircle the wearer's waist. If present, the elasticized side panels will typically be extended and tensioned during this operation so as to conform to the size and shape of the wearer. A pant, such as that shown in FIG. 3, may be placed in position on the wearer by inserting the wearer's legs into the leg openings and sliding the pant into position about the wearer's lower torso. Some pant embodiments may include fastener elements that may be used to secure the pant; generally, the fastener elements are fastened upon application of the pant onto the wearer.

In another embodiment, a plurality of absorbent articles of the present invention may be packaged in a kit. Generally, the kit allows for a quantity of absorbent articles to be delivered to and purchased by a consumer while economizing space and simplifying transport and storage. The kit may require activation so that the article becomes accessible (e.g., opening of a lid, removal of a panel, etc.). In one embodiment, the kit is defined by numerous absorbent articles bound together as an entity and covered by a thermoplastic film overwrap as disclosed in U.S. Pat. No. 5,934,470. The thermoplastic film cover may contain an opening means to allow removal of a portion of the thermoplastic film cover and access to the articles. A typical opening means may include a substantially continuous line of weakness, preferably perforations within the thermoplastic film cover. An exemplary opening means is presented in U.S. Pat. No. 5,036,978.

While one kit embodiment is described above, other variations to the kit are clearly envisioned. The overwrap may comprise a variety of materials including, but not limited to, thermoplastic films, nonwovens, wovens, foils, fabrics, papers, cardboard, elastics, cords, straps, and combinations thereof. The overwrap may completely or partially bind and/or cover the plurality of pull-on garments. Other particularly preferred packages and methods for packaging are disclosed in U.S. Pat. Nos. 5,050,742 and 5,054,619. Furthermore, a kit may contain multiple overwraps. For example, a plurality of pull-on garments of the present inventions may be packaged with a thermoplastic film overwrap and then a plurality of film wrapped pull-on garments being overwrapped in a cardboard box or a second thermoplastic film overwrap. Furthermore, the kit may not contain a dedicated opening means. For example, a thermoplastic film overwrap without perforation may simply be opened by tearing the film.

Test Methods

Post Elongation Recovery

This method is used to determine the post elongation strain of an elastomer as a function of temperature and time. The measurement is done at 22° C. (72° F.) or at 32° C. (90° F.). The measurement at 22° C. (72° F.) is designed to simulate the recovery of the elastomer at room temperature, while the measurement at 32° C. (90° F.) is designed to measure the recovery of the elastomer near skin temperature. A two-step analysis, Stretch and Recovery, is performed on the samples. The method employs a Dynamic Mechanical Analyzer (DMA) such as a TA Instruments DMA 2980 (hereinafter "DMA 2980"), available from TA Instruments, Inc., of New Castle, Del.; equipped with a film clamp, Thermal Advantage/Thermal Solutions software for data acquisition, and Universal Analysis 2000 software for data analysis. Many other types of DMA devices exist, and the use of dynamic mechanical analysis is well known to those skilled in the art of polymer and copolymer characterization.

Methods of operation and calibration and guidelines for using the DMA 2980 are found in TA Instruments DMA 2980 Operator's Manual issued March 2002, Thermal Advantage User's Reference Guide issued July 2000 and Universal Analysis 2000 guide issued February 2003. To those skilled in the use of the DMA 2980, the following operational run conditions should be sufficient to replicate the stretch and recovery of the samples.

The experimental conditions are selected on the DMA 2980 which specify operation in the Controlled Force Mode with the film clamp. The film clamp is mounted onto the DMA 2980 and calibrated according to the User's Reference Guide. The material to be tested is cut into samples of substantially uniform dimension. Appropriate sample dimensions may be selected to achieve the required strain. For the DMA 2980, suitable sample dimensions are approximately 6.4 mm wide by approximately 0.15 mm thick. The lower film clamp of the DMA 2980 is adjusted and locked in a position which provides approximately 6 mm between the clamping surfaces. The sample is mounted in the film clamps and the lower clamp is allowed to float to determine the actual gauge length between the film clamps. The sample ID and dimensions are recorded. The film clamp is locked in position, and the furnace is closed.

Stretch Method—Specific DMA 2980 parameter settings for the above sample dimensions are set as follows: Preload force applied to sample in clamp (0.01N); auto zero displacement (on) at the start of the test; furnace (close), clamp position (lock), and temperature held at $T_i$ (22° C. or 32° C.) at the end of the stretch method. Data acquisition rate is set at 0.5 Hz (1 point per 2 seconds). The stretch method is loaded onto the DMA 2980. The method segments are (1) Initial Temperature $T_i$ (22° C. or 32° C.), (2) Equilibrate at $T_i$ (3) Data Storage ON, and (4) Ramp Force 5.0 N/min to 18.0 N.

Upon initiation of the test, the temperature ramps to the specified $T_i$ (22° C. or 32° C.) [method segment 1], and the temperature is maintained at this $T_i$ [method segment 2]. After a minimum of 15 minutes at $T_i$, the operator initiates the sample stretching and concurrent data collection [method segments 3 and 4]. The sample is stretched with an applied ramp force of 5 N per minute to approximately 30 mm in length. The gradual increase in force more closely simulates application of the article and prevents sample breakage. The sample is locked in place at the stretched length of approximately 30 mm and maintained at $T_i$. The force required to reach the 400% strain is recorded manually from the digital readout on the instrument.

For samples of different dimensions, the applied force is adjusted to achieve an applied ramp force of 5 N/min per square millimeter of initial sample cross-sectional area; and the maximum displacement is adjusted to achieve a strain of 400%. The percent strain is calculated by subtracting the gauge length from the stretched length, then dividing the result by the gauge length and multiplying by 100. A sample stretched from an initial length of 6 mm to a length of 30 mm results in a 400% strain.

Recovery Method—The Recovery Method is loaded onto the instrument and initiated approximately 15 seconds after reaching the desired initial percent strain (400%) in the Stretch Method. The four segments of the recovery method are (1) Data Storage ON, (2) Force 0.01 N, (3) Ramp to $T_i$, and (4) Isotherm for 3.0 minutes. The following DMA 2980 parameter setting is changed from the Stretch Method: auto zero displacement is changed to (OFF). The Recovery Method measures the length of the sample over a 3 minute time period at the specified temperature ($T_i$=either 22° C. or 32° C.). The sample length, percent strain, and test temperature are recorded as a function of recovery time. The post elongation strain is reported as percent strain after different times of recovery (15 seconds, 30 seconds, 60 seconds, and 3 minutes).

For different sample dimensions, the force applied to the sample during recovery (segment 2 above) is adjusted to achieve an applied force of 0.01 N per square millimeter of initial sample cross-sectional area (determined prior to stretching the sample).

Two Cycle Hysteresis Test

This method is used to determine properties that may correlate with the forces experienced by the consumer during application of the product containing the slow recovery elastomer and how the product fits and performs once it is applied.

The two cycle hysteresis test method is performed at room temperature (21° C./70° F.) and also at body temperature (37° C./99° F.). The material to be tested is cut into samples of substantially rectilinear dimensions. Sample dimensions should be selected to achieve the required strain with forces appropriate for the instrument. Suitable instruments for this test include tensile testers commercially available from MTS Systems Corp., Eden Prairie, Minn. (e.g. Alliance RT/1 or Sintech 1/S) or from Instron Engineering Corp., Canton, Mass. For either the Alliance RT/1 or Sintech 1/S instruments listed above, suitable sample dimensions are approximately 0.13 mm thick, approximately 20 mm wide by approximately 100 mm long.

The following procedure illustrates the measurement when using the above sample dimensions and either an Alliance RT/1 or Sintech 1/S. The instrument is interfaced with a computer. TestWorks 4™ software controls the testing parameters, performs data acquisition and calculation, and provides graphs and data reports.

The grips used for the test are equal to or wider than the width of the sample. Typically 1" (2.54 cm) wide grips are used. The grips are air actuated grips designed to concentrate the entire gripping force along a single line perpendicular to the direction of testing stress having one flat surface and an opposing face from which protrudes a half round (radius=6 mm) to minimize slippage of the sample. In the case of the measurement at 37° C., the upper grip is a lightweight grip with serrated faces.

The load cell is selected so that the forces measured will be between 10% and 90% of the capacity of the load cell or the load range used. Typically a 25 N load cell is used. The fixtures and grips are installed. The instrument is calibrated according to the manufacturer's instructions. The distance between the lines of gripping force (gauge length) is 2.50" (63.5 mm), which is measured with a steel ruler held beside the grips. The load reading on the instrument is zeroed to account for the mass of the fixture and grips. The mass and thickness of the specimen are measured before testing. The specimen is mounted into the grips in a manner such that there is no slack and the load measured is between 0.00 N and 0.02 N. After being mounted in the grips, the sample is equilibrated at the testing temperature for 5 minutes before starting the test. A suitable environmental chamber is used to maintain the temperature at 37° C. for measurements performed at this temperature. The instrument is located in a temperature-controlled room for measurements performed at 21° C.

The 2 cycle hysteresis test method involves the following steps:

(1) Strain the sample to the specified maximum percent strain (i.e., $Strain_{max}$=150%) at a constant crosshead speed of 20"/min. (50.8 cm/min) with no hold.

(2) Reduce the strain to 0% strain (i.e., return grips to original gauge length of 2.50") at a constant crosshead speed of 3"/min. (7.62 cm/min) with no hold.

(3) Strain the sample to $Strain_{max}$ at a constant crosshead speed of 20"/min. (50.8 cm/min) with no hold.

(4) Reduce strain to 60% strain at a constant crosshead speed of 3"/min. (7.62 cm/min)

(5) Hold the sample at 60% strain for 5 minutes.

(6) Go to 0% strain at a constant crosshead speed 3"/min. (7.62 cm/min)

The measured unload force is the measured unload force of the sample at 60% strain after the 5 minute hold in step 5. This force is normalized to Newtons per square millimeter of initial sample cross-sectional area (determined before the sample is stretched) as follows: Normalized unload force=measured unload force÷[initial sample thickness in mm×initial sample width in mm]

For different sample dimensions, the crosshead speed is adjusted to maintain the appropriate strain rate for each portion of the test. For example, a crosshead speed of 10"/min (25.4 cm/min) would be used in Steps 1 and 3 for a sample gauge length of 1.25" (31.7 mm).

EXAMPLES

Films of the slow recovery elastomeric composition are prepared by blending varying amounts of elastomeric polymer, modifying resin and mineral oil as shown in Table 1. The blending is accomplished by extrusion of the mixture (Examples 2 and 3) or by solvent casting the mixture and pressing into a film on a heated Carver Press (Examples 1, 4, 5, 6 and 7). The amount of each component is expressed in weight percent of the elastomeric composition. The examples in Table 1 comprise a triblock elastomeric copolymer, styrene-isoprene-styrene (S-I-S), commercially available under the trade designation Vector 4211 from Dexco Polymers L.P., Houston, Tex. In some examples (Examples 2, 3, 4, 6 and 7), a component of the elastomeric composition is white mineral oil, commercially available under the trade designation Britol® 50T from Crompton Corporation, Petrolia, Pa. Modifying resins suitable for use that are disclosed in the examples in Table 1 are an alicyclic hydrocarbon resin under the trade designation Arkon P140 (Tg of 86° C.), available from Arakawa Chemical Inc., Chicago, Ill., and poly(t-butyl styrene) (Tg of 126° C. and 130° C. for the 14 kDa and 19 kDa molecular weight resins, respectively), synthesized at Procter & Gamble Company via free radical polymerization of t-butylstyrene monomer available from Aldrich Chemical Company, St. Louis, Mo.

TABLE 1

| | Elastomeric Composition (Weight %) | | | | | | |
|---|---|---|---|---|---|---|---|
| | Sample | | | | | | |
| | 1 | 2 | 3 | 4 | 5 | 6 | 7 |
| Vector 4211 (SIS, 29% S) | 100 | 45 | 45 | 49 | 60 | 59 | 45 |
| Poly(t-butyl styrene), 14 kDa | | 45 | | | | | |
| Poly(t-butyl styrene), 19 kDa | | | 45 | | 40 | 39 | 45 |
| Arkon P140 | | | | 49 | | | |
| Mineral Oil, White Britol-50T | | 10 | 10 | 2 | | 2 | 10 |

Sample 1 is a comparative example whereas Sample 2–7 are embodiments of the present invention.

The weight average molecular weights of the poly(t-butylstyrene) samples are 14 and 19 kDa as determined by gel permeation chromatography using polystyrene standards in tetrahydrofuran.

Films of the elastomeric compositions in Table 1 are measured according to the Post Elongation Recovery method described in the Test Methods section above. The thickness of the film tested and the force (not normalized for film thickness) in Newtons to strain the sample to 400% strain are shown in Table 2. The post elongation strain is reported at different recovery times (15 seconds, 30 seconds, 60 seconds, and 3 minutes).

TABLE 2

Post Elongation Strains of Films of the Elastomeric Compositions of Table 1

| | Sample | | | | | | |
|---|---|---|---|---|---|---|---|
| | 1 | 2 | 3 | 4 | 5 | 6 | 7 |
| Post Elongation Strain at 22° C. (72° F.) | | | | | | | |
| Film Thickness (mm) | 0.16 | 0.13 | 0.14 | 0.14 | 0.16 | 0.16 | 0.13 |
| % Strain after 15 seconds recovery | 13 | 137 | 178 | 102 | 153 | 104 | 157 |
| % Strain after 30 seconds recovery | 13 | 98 | 141 | 73 | 117 | 71 | 122 |
| % Strain after 60 seconds recovery | 12 | 64 | 105 | 50 | 88 | 44 | 88 |
| % Strain after 3 minutes recovery | 11 | 29 | 59 | 28 | 48 | 19 | 48 |
| Force (N) | 2.5 | 1.0 | 1.3 | 1.1 | 1.7 | 1.1 | 1.2 |
| Post Elongation Strain at 32° C. (90° F.) | | | | | | | |
| Film Thickness (mm) | 0.15 | 0.14 | 0.13 | 0.14 | 0.16 | 0.14 | 0.14 |
| % Strain after 15 seconds recovery | 16 | 43 | 109 | 41 | 58 | 56 | 81 |
| % Strain after 30 seconds recovery | 15 | 24 | 74 | 27 | 37 | 34 | 53 |
| % Strain after 60 seconds recovery | 15 | 13 | 46 | 18 | 23 | 21 | 33 |
| % Strain after 3 minutes recovery | 14 | 7 | 19 | 11 | 11 | 11 | 16 |
| Force (N) | 1.8 | 0.6 | 0.7 | 0.7 | 1.0 | 0.7 | 0.8 |

The normalized unload forces of films of the elastomeric compositions in Table 1 are measured at 21° C. and 37° C. according to the 2-Cycle Hysteresis Test described in the Test Methods Section above. The data are shown in Table 3.

TABLE 3

Normalized Unload Forces (N/mm$^2$) of Films of the Elastomeric Compositions of Table 1

| | Sample | | | | | | | |
|---|---|---|---|---|---|---|---|---|
| | 1 | 2 | 3 | 4 | 5 | 6 | 7 | 8[1] |
| Normalized Unload Force at 21° C. (70° F.) [N/mm$^2$] | 0.50 | 0.06 | 0.08 | 0.13 | 0.15 | 0.17 | 0.10 | N.A. |
| Normalized Unload Force at 37° C. (99° F.) [N/mm$^2$] | 0.63 | 0.08 | 0.08 | 0.12 | 0.14 | 0.16 | 0.10 | 0.03 |

[1]Sample No. 8 is a comparative example of Findley H2401 adhesive (pressed into a film using a heated Carver Press).

All documents cited in the Detailed Description of the Invention are, in relevant part, incorporated herein by reference; the citation of any document is not to be construed as an admission that it is prior art with respect to the present invention. To the extent that any definition or meaning of a term in this written document conflicts with any definition or meaning of the term in a document incorporated by reference, the definition or meaning assigned to the term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article having at least one stretch zone comprising a slow recovery elastomer wherein:
   a) said slow recovery elastomer exhibits a normalized unload force of greater than 0.04 N/mm$^2$ at 37° C.; and
   b) said slow recovery elastomer exhibits at least 50% post elongation strain at 22° C. after 15 seconds of recovery from a 400% strain; and
   c) said stretch zone is a linear stretch zone or a curvilinear stretch zone.

2. The absorbent article of claim 1 further comprising at least a second stretch zone comprising a traditional elastomer.

3. The absorbent article of claim 1 wherein the slow recovery elastomer exhibits a post elongation strain of at least 40% after 60 seconds of recovery at 22° C.

4. The absorbent article of claim 1 wherein the slow recovery elastomer exhibits a post elongation strain from 100% to 150% after 15 seconds of recovery at 22° C.

5. The absorbent article of claim 1 wherein the post elongation strain of the slow recovery elastomer after 15 seconds of recovery at 22° C. minus the post elongation strain of said slow recovery elastomer after 15 seconds of recovery at 32° C. is at least 35%.

6. The absorbent article of claim 1 wherein the slow recovery elastomer is in a form selected from the group consisting of strands, films, bands, strands, fibers, or combinations thereof.

7. The absorbent article of claim 1, wherein said absorbent article has a longitudinal centerline and a lateral centerline and said absorbent article further comprises at least one feature selected from the group consisting of a topsheet, a liquid impermeable backsheet, an absorbent core, an ear, a side panel, a waist feature, a fastener component, a leg cuff, a gasketing cuff, a barrier cuff, and combinations thereof; wherein said feature comprises at least a part of said stretch zone.

8. The absorbent article of claim 7 wherein the stretch zone is a linear stretch zone disposed at an angle of between −70° and +70° with respect to said lateral centerline.

9. The absorbent article of claim 7 wherein the absorbent article comprises at least two linear stretch zones, said linear stretch zones being disposed at different angles with respect to said lateral centerline.

10. The absorbent article of claim 9 wherein the absorbent article comprises a first linear stretch zone disposed at an angle between 0° and +50° with respect to said lateral centerline and a second linear stretch zone disposed at an angle between 0° and −50° with respect to said lateral centerline.

11. The absorbent article of claim 1 wherein the stretch zone is a curvilinear stretch zone, at least a portion of said curvilinear stretch zone has a radius of curvature between 1 mm and 1 m.

12. The absorbent article of claim 1 wherein the stretch zone has a width dimension of at least 0.2 mm.

13. The absorbent article of claim 1 wherein the stretch zone has a thickness dimension of at least 0.1 mm.

14. The absorbent article of claim 1 wherein the absorbent article comprises at least two stretch zones; wherein at least one said stretch zone comprises the slow recovery elastomer and the other stretch zone comprises an elastomeric composition differing from the slow recovery elastomer in a property selected from the group consisting of normalized unload force at 37° C., post elongation strain at 22° C. after 15 seconds of recovery from a 400% strain, or both.

15. The absorbent article of claim 1 comprising a plurality of stretch zones in an array; said plurality of stretch zones having a spacing therebetween and said spacing is selected from the group consisting of uniform spacing and non-uniform spacing.

16. The absorbent article of claim 1 wherein said absorbent article comprises a first plurality of stretch zones in a first array and a second plurality of stretch zones in a second array.

17. The absorbent article of claim 16 wherein the first plurality of stretch zones in the first array have a first spacing and the second plurality of stretch zones in the second array have a second spacing; wherein the first spacing and second spacing are not equal.

18. The absorbent article of claim 16 wherein the first plurality of stretch zones comprise a first slow recovery elastomer and the second plurality of stretch zones comprise a second slow recovery elastomer, wherein the first slow recovery elastomer and second slow recovery elastomer differ in a property selected from the group consisting of normalized unload force at 37° C., post elongation strain at 22° C. after 15 seconds of recovery from a 400% strain, or both.

19. An absorbent article of claim 1 wherein said absorbent article is a disposable diaper.

20. The absorbent article of claim 1 wherein the slow recovery elastomer exhibits a post elongation strain of from 75% to 150% after 15 seconds of recovery at 22° C.

21. The absorbent article of claim 1 wherein the slow recovery elastomer exhibits a post elongation strain of greater than 150% after 15 seconds of recovery at 22° C.

22. An absorbent article having at least one stretch zone comprising a slow recovery elastomer wherein:
a) said slow recovery elastomer exhibits a normalized unload force of greater than 0.04 N/mm² at 37° C.; and
b) a post elongation strain of said slow recovery elastomer after 15 seconds of recovery at 22° C. minus the post elongation strain of said slow recovery elastomer after 15 seconds of recovery at 32° C. is at least 35%; and
c) said stretch zone is a linear stretch zone or a curvilinear stretch zone.

* * * * *